(12) United States Patent
Del Rossi et al.

(10) Patent No.: US 12,017,064 B2
(45) Date of Patent: Jun. 25, 2024

(54) BIOELECTRIC DEVICES FOR USE ON SPECIFIC AREAS OF THE BODY

(71) Applicant: Vomaris Innovations, Inc., Tempe, AZ (US)

(72) Inventors: Joseph Del Rossi, Tempe, AZ (US); Troy Paluszcyk, Tempe, AZ (US)

(73) Assignee: Vomaris Innovations, Inc., Fountain Hills, AZ (US)

(*) Notice: Subject to any disclaimer, the term of this patent is extended or adjusted under 35 U.S.C. 154(b) by 616 days.

(21) Appl. No.: 17/209,004

(22) Filed: Mar. 22, 2021

(65) Prior Publication Data
US 2021/0228863 A1 Jul. 29, 2021

Related U.S. Application Data

(63) Continuation of application No. 16/078,419, filed as application No. PCT/US2017/020109 on Mar. 1, 2017, now Pat. No. 10,980,995.

(60) Provisional application No. 62/301,830, filed on Mar. 1, 2016.

(51) Int. Cl.
*A61N 1/04* (2006.01)
*A61F 13/00* (2006.01)
*A61N 1/20* (2006.01)

(52) U.S. Cl.
CPC ............ *A61N 1/0492* (2013.01); *A61F 13/00* (2013.01); *A61F 13/00051* (2013.01); *A61N 1/0468* (2013.01); *A61N 1/0476* (2013.01); *A61N 1/205* (2013.01)

(58) Field of Classification Search
CPC .. A61N 1/0492; A61N 1/0468; A61N 1/0476; A61N 1/205
See application file for complete search history.

(56) References Cited

U.S. PATENT DOCUMENTS

| 4,635,641 A | 1/1987 | Hoffman | |
| 2005/0192636 A1* | 9/2005 | Skiba | A61N 1/303 607/2 |
| 2010/0331811 A1* | 12/2010 | Imran | A61N 1/0436 604/501 |
| 2015/0223988 A1 | 8/2015 | Spector | |

FOREIGN PATENT DOCUMENTS

| WO | 2015187858 | 12/2015 |
| WO | 2017151715 | 9/2017 |

OTHER PUBLICATIONS

International Search Report and Written Opinion PCT/US17/20109 dated May 24, 2017.

* cited by examiner

*Primary Examiner* — Amanda K Hulbert
*Assistant Examiner* — Philip C Edwards
(74) *Attorney, Agent, or Firm* — K&L Gates LLP; Louis C. Cullman; Hal Gibson

(57) ABSTRACT

A bioelectric device includes multiple first reservoirs and multiple second reservoirs joined with a planar substrate. Selected ones of the multiple first reservoirs include a reducing agent, and first reservoir surfaces of selected ones of the multiple first reservoirs are proximate to a first substrate surface. Selected ones of the multiple second reservoirs include an oxidizing agent, and second reservoir surfaces of selected ones of the multiple second reservoirs are proximate to the first substrate surface.

14 Claims, 13 Drawing Sheets

BIOELECTRIC DEVICES FOR USE ON SPECIFIC AREAS OF THE BODY

RELATED APPLICATIONS

This application is a continuation of U.S. patent application Ser. No. 16/078,419 filed on Aug. 21, 2018, which is an application under 35 U.S.C. § 371 of International Patent Application PCT/US2017/020109 filed on Mar. 1, 2017, which claims the benefit of U.S. Provisional Patent Application No. 62/301,830, filed Mar. 1, 2016; the disclosure of which is incorporated herein by reference in its entirety.

FIELD

The present specification relates to bioelectric devices designed for improved performance on specific areas of the body, for example on or around joints or other contoured areas, and methods of manufacture and use thereof.

BACKGROUND

Biologic tissues and cells are affected by electrical stimulus. The present Specification relates to systems, methods and devices useful for applying electric fields and/or currents to a treatment area.

SUMMARY

Disclosed herein are systems, devices, and methods for use in treatment of subjects, in particular treatment of specific areas of tissue, for example around or about a specific feature or joint of the body, for example the nose, the eye, the ear, the knee, the elbow, the shoulder, or on an area of gentler contours, such as the back or the hip or the thigh, or the like. Certain embodiments are designed for universal conformability with multiple areas of the body, for example a flat area, a contoured area, a rippled area, or the like.

In embodiments, the systems, devices, and methods include substrates, for example dressings, for example bandages, that comprise one or more biocompatible electrodes configured to generate at least one of a low level electric field (LLEF) or low level electric current (LLEC). Embodiments disclosed herein can produce a uniform current or field density. In embodiments the dressings are configured to conform to the area to be treated, for example by producing the dressing in particular shapes including "slit" or discontinuous regions. In embodiments the dressing can be produced in a U shape wherein the "arms" of the U are substantially equal in length as compared to the "base" of the U. In embodiments the dressing can be produced in a U shape wherein the "arms" of the U are substantially longer in length as compared to the "base" of the U. In embodiments the dressing can be produced in a U shape wherein the "arms" of the U are substantially shorter in length as compared to the "base" of the U. In embodiments the dressing can be produced in an X shape wherein the "arms" of the X are substantially equal in length.

In certain embodiments, the substrate comprising the multi-array matrix can comprise one layer of a composite dressing, for example a composite wound dressing comprising the substrate, an adhesive layer, an absorbent layer (expandable in embodiments), and a film layer. In embodiments, the film layer is stretchable. In embodiments, the film layer is expandable.

The systems and devices can comprise corresponding or interlocking perimeter areas to assist the devices in maintaining their position on the patient and/or their position relative to each other. In certain embodiments, the systems and devices can comprise a port or ports to provide access to the treatment area beneath the device.

Certain embodiments can comprise a solution or formulation comprising an active agent and a solvent or carrier or vehicle.

Disclosed embodiments conform comfortably to a number of areas of the body, for example, joints, and can be used to cover wide range of incisions. For example, disclosed embodiments can be used following total shoulder arthroplasty (TSA), and provide pain-free, unrestricted mobility through a wide range of motion.

DETAILED DESCRIPTION

Figure 1:
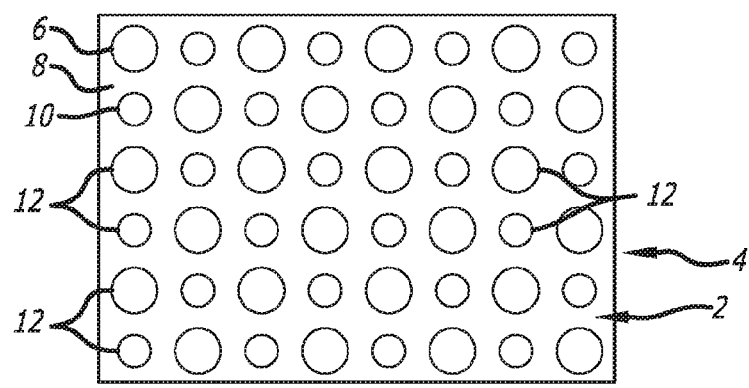
FIG. 1 depicts a detailed plan view of a substrate layer microcell pattern disclosed herein.

Disclosed herein are substrates, for example wound dressings such as bandages, that are shaped to complement specific areas of the body, for example the anatomy of a protuberance or a joint, for example by designing the perimeter of the dressing to incorporate slits and/or specific shapes that enable the dressing to better conform to a 3D surface, in some embodiments throughout a range of motion. Joints may be classified functionally based upon how much movement they allow. A joint that permits no movement is known as a synarthrosis. The sutures of the skull and the gomphoses that connect the teeth to the skull are examples of synarthroses.

An amphiarthrosis allows a slight amount of movement at the joint. Examples of amphiarthroses include the intervertebral disks of the spine and the pubic symphysis of the hips.

The third functional class of joints is the freely movable diarthrosis joints. Diarthroses have the highest range of motion of any joint and include the elbow, knee, shoulder, and wrist.

Joints may also be classified structurally based upon what kind of material is present in the joint. Fibrous joints are made of tough collagen fibers and include the sutures of the skull and the syndesmosis joint that holds the ulna and radius of the forearm together. Cartilaginous joints are made of a band of cartilage that binds bones together. Some examples of cartilaginous joints include joints between the ribs and costal cartilage, and the intervertebral disks of the spine. The most common type of joint, the synovial joint, features a fluid-filled space between smooth cartilage pads at the end of articulating bones. Surrounding the joint is a capsule of tough dense irregular connective tissue lined with synovial membrane. The outer layer of capsule may extend into thick, strong bands called ligaments that reinforce the joint and prevent undesired movements and dislocations. Synovial membrane lining the capsule produces the oily synovial fluid that lubricates the joint and reduces friction and wear.

There are many different classes of synovial joints in the body, including gliding, hinge, saddle, and ball and socket joints. Gliding joints, such as the ones between the carpals of the wrist, are found where bones meet as flat surfaces and allow for the bones to glide past one another in any direction. Hinge joints, such as the elbow and knee, limit movement in only one direction so that the angle between bones can increase or decrease at the joint. The limited motion at hinge joints provides for more strength and reinforcement from the bones, muscles, and ligaments that make up the joint. Saddle joints, such as the one between the first metacarpal and trapezium bone, permit 360-degree motion by allowing the bones to pivot along two axes. The shoulder and hip joints form the only ball and socket joints in the body. These joints have the freest range of motion of any joint in the body—they are the only joints that can move in a full circle and rotate around their axis.

Embodiments disclosed herein can comprise systems, devices, and methods for use in treating any joint of the body, for example a fibrous, cartilaginous, synarthrotic, or synovial joint.

Disclosed systems, devices, and methods comprise wound dressings that can reduce or eliminate painful shear force caused by standard dressings. Certain embodiments can also allow for improved/complete articulation of the treated joint, for example the knee or elbow.

Embodiments can comprise a non-restrictive adhesive layer. Embodiments can comprise elongated areas, or "flanges" to wrap around the treatment area surrounding the treated joint.

A dressing disclosed herein and placed over tissue such as a joint can move relative to the tissue. Reducing the amount of motion between tissue and dressing can be advantageous to healing. In embodiments, traction or friction blisters can be treated, minimized, or prevented. The use of the dressing as a temporary "bridge" to reduce stress across the wound site can reduce stress at the sutures or staples and this will reduce scarring and encourage healing.

Disclosed herein are wound dressings, for example bandages, that are shaped to "universally" complement many areas of the body, for example by designing the perimeter of the dressing to incorporate slits and/or specific shapes that enable the dressing to better conform to a 3D surface. For example, such embodiments can be used on the back, the shoulder, the chest, the stomach, the buttocks, the hip, the calf, the thigh, or the like.

Embodiments disclosed herein comprise methods, systems and devices that can provide a low level electric field to a treatment area or, when brought into contact with an electrically conducting material, can provide a low level electric current to a treatment area. Thus, in embodiments an LLEC system is an LLEF system that is in contact with an electrically conducting material, for example a liquid material. In certain embodiments, the micro-current or electric field can be modulated, for example, to alter the duration, size, shape, field depth, duration, current, polarity, or voltage of the system. For example, it can be desirable to employ an electric field of greater strength or depth in a particular treatment area to achieve optimal treatment. In embodiments the watt-density of the system can be modulated.

Aspects disclosed herein comprise composite devices that can comprise a multi-array matrix on a substrate layer, for example a planar substrate layer. Such matrices can include a first array comprising a pattern of microcells formed from a first conductive solution, the first solution comprising a metal species; and a second array comprising a pattern of microcells formed from a second conductive solution, the second solution comprising a metal species capable of defining at least one voltaic cell for spontaneously generating at least one electrical current with the metal species of the first array when said first and second arrays are introduced to an electrolytic solution and said first and second arrays are not in physical contact with each other. Certain aspects utilize an external power source such as AC or DC power or pulsed RF or pulsed current, such as high voltage pulsed current. In one embodiment, the electrical energy is derived from the dissimilar metals creating a battery at each cell/cell interface, whereas those embodiments with an external power source can require conductive electrodes in a spaced apart configuration to predetermine the electric field shape and strength.

Embodiments disclosed herein can comprise an expandable absorbent layer that can absorb excess fluid from the substrate and expand away from the treatment area, thus preventing oversaturation of the treatment area with resultant maceration and increased infection risk. Embodiments disclosed herein can comprise a non-expandable absorbent layer.

Embodiments can comprise a stretchable, expandable film layer that can stretch to accommodate a larger volume as the expandable absorbent layer absorbs liquid. This aspect can be mechanically decoupled from the adhesive layer in order to reduce shear forces on the skin. Additionally, the vertically-expanding absorbent layer and film allows the dressing to absorb more volume of fluid in a smaller contact area ("footprint").

Definitions

"Active agent" as used herein means an ingredient or drug that is biologically active and can be present in a formulation or solution. Some formulations can contain more than one active ingredient.

"Affixing" as used herein can mean contacting a patient or tissue with a device or system disclosed herein. In embodiments "affixing" can comprise the use of straps, elastic, adhesive, etc.

"Applied" or "apply" as used herein refers to contacting a surface with a conductive material, for example printing, painting, or spraying a conductive ink on a surface. Alternatively, "applying" can mean contacting a treatment area with a device or system disclosed herein.

"Conductive material" as used herein refers to an object or type of material which permits the flow of electric charges in one or more directions. Conductive materials can comprise solids such as metals or carbon, or liquids such as conductive metal solutions and conductive gels. Conductive materials can be applied to form at least one matrix. Conductive liquids can dry, cure, or harden after application to form a solid material. Solid material can also be cast from a polymer solution that contains conductive material and water wherein the water evaporates when the conductive liquids dry, cure, or harden. Solid material can then be activated when soaked in water for use.

"Cosmetic product" as used herein refers to substances used to enhance the appearance of the body. They are generally mixtures of chemical compounds, some being derived from natural sources, many being synthetic. These products are generally liquids or creams or ointments intended to be applied to the human body for cleansing, beautifying, promoting attractiveness, or altering the appearance. These products can be electrically conductive.

"Discontinuous region" as used herein refers to a "void" in a material such as a hole, slit, slot, or the like. The term can mean any void in the material though typically the void is of a regular shape. A void in the material can be enclosed entirely within the perimeter of a material or it can extend to the perimeter of a material.

"Dots" as used herein refers to discrete deposits of similar or dissimilar reservoirs that can, in certain embodiments, function as at least one battery cell. The term can refer to a deposit of any suitable size or shape, such as squares, circles, triangles, lines, etc. The term can be used synonymously with, microcells, microspheres, etc. "Microspheres" refers to small spherical particles, with diameters in the micrometer range (typically 1 µm to 1000 µm (1 mm)). Microspheres are sometimes referred to as microparticles. Microspheres can be manufactured from various natural and synthetic materials. The term can be used synonymously with, microballoons, beads, particles, etc.

"Electrode" refers to similar or dissimilar conductive materials. In embodiments utilizing an external power source the electrodes can comprise similar conductive materials. In embodiments that do not use an external power source, the electrodes can comprise dissimilar conductive materials that can define an anode and a cathode.

"Expandable" as used herein refers to the ability to stretch while retaining structural integrity and not tearing. The term can refer to solid regions as well as discontinuous or void regions; solid regions as well as void regions can stretch or expand. "Expandable" can refer to stretching along any axis, including the "Z" axis, that is, wherein the dressing expands away from the treatment site while maintaining contact with the treatment site.

"Interlocking" as used herein refers to areas on the perimeter of disclosed devices that complement other areas on the perimeter such that the areas engage with each other by the fitting together of projections and recesses. This design can enable disclosed devices to "nest" closely together to treat multiple areas in close proximity to one another.

"Matrix" or "matrices" as used herein refer to a pattern or patterns, such as those formed by electrodes on a surface, such as a fabric or a fiber or microparticle, or the like. Matrices can also comprise a pattern or patterns within a solid or liquid material or a three dimensional object. Matrices can be designed to vary the electric field or electric current or microcurrent generated. For example, the strength and shape of the field or current or microcurrent can be altered, or the matrices can be designed to produce an electric field(s) or current or microcurrent of a desired strength or shape.

"Reduction-oxidation reaction" or "redox reaction" as used herein refers to a reaction involving the transfer of one or more electrons from a reducing agent to an oxidizing agent. The term "reducing agent" can be defined in some embodiments as a reactant in a redox reaction, which donates electrons to a reduced species. A "reducing agent" is thereby oxidized in the reaction. The term "oxidizing agent" can be defined in some embodiments as a reactant in a redox reaction, which accepts electrons from the oxidized species. An "oxidizing agent" is thereby reduced in the reaction. In various embodiments a redox reaction produced between a first and second reservoir provides a current between the dissimilar reservoirs. The redox reactions can occur spontaneously when a conductive material is brought in proximity to first and second dissimilar reservoirs such that the conductive material provides a medium for electrical communication and/or ionic communication between the first and second dissimilar reservoirs. In other words, in an embodiment electrical currents can be produced between first and second dissimilar reservoirs without the use of an external battery or other power source (e.g., a direct current (DC) such as a battery or an alternating current (AC) power source such as a typical electric outlet). Accordingly, in various embodiments a system is provided which is "electrically self contained," and yet the system can be activated to produce electrical currents. The term "electrically self contained" can be defined in some embodiments as being capable of producing electricity (e.g., producing current) without an external battery or power source. The term "activated" can be defined in some embodiments to refer to the production of electric current through the application of a radio signal of a given frequency or through ultrasound or through electromagnetic induction.

"Stretchable" as used herein refers to the ability of embodiments that stretch without losing their structural integrity. That is, embodiments can stretch to accommodate irregular skin surfaces or surfaces wherein one portion of the surface can move relative to another portion.

"Universal" as used herein refers to the ability of disclosed embodiments to conform to a number of different areas of the body.

Systems, Devices, and Methods of Manufacture

In embodiments, systems and devices disclosed herein comprise a substrate layer comprising patterns of electrodes or micro-batteries that create an electric field between each dot pair. In embodiments, the field is very short, e.g. in the range of physiologic electric fields. In embodiments, the direction of the electric field produced by devices disclosed herein is omnidirectional within a three dimensional material. In a further exemplary embodiment, systems and devices disclosed herein comprise a substrate layer comprising patterns of electrodes or micro-batteries that create an electric field between each dot pair. In embodiments, the field is very short, e.g. in the range of physiologic electric fields. In embodiments, the direction of the electric field produced by devices disclosed herein is omnidirectional within a three dimensional material.

Embodiments disclosed herein can comprise multiple layers. For example, an embodiment can comprise a substrate layer comprising a multi-array matrix; an adhesive layer; an expandable absorbent layer; a film layer, and the like. Embodiments can be ETO and Gamma Sterilization compatible.

Substrate layers as disclosed herein can comprise absorbent or non-absorbent textiles, low-adhesives, vapor permeable films, hydrocolloids, hydrogels, alginates, foams, foam-based materials, cellulose-based materials comprising Kettenbach fibers, hollow tubes, fibrous materials, such as those impregnated with anhydrous/hygroscopic materials, beads and the like, or any suitable material as known in the art.

In embodiments, the substrate layer can comprise electrodes or microcells. Each electrode or microcell can be or comprise a conductive metal. In embodiments, the electrodes or microcells can comprise any electrically-conductive material, for example, an electrically conductive hydrogel, metals, electrolytes, superconductors, semiconductors, plasmas, and nonmetallic conductors such as graphite and conductive polymers. Electrically conductive metals can comprise silver, copper, gold, aluminum, molybdenum, zinc, lithium, tungsten, brass, carbon, nickel, iron, palladium, platinum, tin, bronze, carbon steel, lead, titanium, stainless steel, mercury, Fe/Cr alloys, and the like. The electrodes can be solid, coated or plated with a different metal such as aluminum, gold, platinum or silver.

In certain embodiments, reservoir or electrode geometry can comprise circles, polygons, lines, zigzags, ovals, stars, or any suitable variety of shapes. This provides the ability to design/customize surface electric field shapes as well as depth of penetration. For example. In embodiments it can be desirable to employ an electric field of greater strength or depth in an area where skin is thicker to achieve optimal treatment. In another embodiment, the desirable strength of an electric field be employed within a three dimensional material such as a hydrogel or solid object.

Reservoir or electrode or dot sizes and concentrations can vary, as these variations can allow for changes in the properties of the electric field created by embodiments of the invention. Certain embodiments provide an electric field at about 1 Volt and then, under normal tissue loads with resistance of 100k to 300K ohms, produce a current in the range of 10 microamperes. The electric field strength can be determined by calculating % the separation distance and applying it in the z-axis over the midpoint between the cells.

In other embodiments, a system can be provided which comprises an external battery or power source. For example, an AC power source can be of any wave form, such as a sine wave, a triangular wave, or a square wave. AC power can also be of any frequency such as for example 50 Hz or 60 HZ, or the like. AC power can also be of any voltage, such as for example 120 volts, or 220 volts, or the like. In embodiments an AC power source can be electronically modified, such as for example having the voltage reduced, prior to use.

In embodiments, systems and devices disclosed herein can apply an electric field, an electric current, or both, wherein the field, current, or both can be of varying size, strength, density, shape, or duration in different areas of the embodiment. In embodiments, systems and devices disclosed herein can apply an electric field, an electric current, or both, wherein the field, current, or both can be of uniform size, strength, density, shape, or duration. In embodiments, by micro-sizing the electrodes or reservoirs, the shapes of the electric field, electric current, or both can be customized, increasing or decreasing very localized watt densities and allowing for the design of patterns of electrodes or reservoirs wherein the amount of electric field over a tissue can be designed or produced or adjusted based upon feedback from the tissue or upon an algorithm within sensors operably connected to the embodiment and a control module. The electric field, electric current, or both can be stronger in one zone and weaker in another. The electric field, electric current, or both can change with time and be modulated based on treatment goals or feedback from the tissue or patient. The control module can monitor and adjust the size, strength, density, shape, or duration of electric field or electric current based on material parameters or tissue parameters. For example, embodiments disclosed herein can produce and maintain very localized electrical events. For example, embodiments disclosed herein can produce specific values for the electric field duration, electric field size, electric field shape, field depth, current, polarity, and/or voltage of the device or system.

In various embodiments the difference of the standard potentials of the electrodes or dots or reservoirs can be in a range from about 0.05 V to approximately about 5.0 V. For example, the standard potential can be about 0.05 V, about 0.06 V, about 0.07 V, about 0.08 V, about 0.09 V, about 0.1 V, about 0.2 V, about 0.3 V, about 0.4 V, about 0.5 V, about 0.6 V, about 0.7 V, about 0.8 V, about 0.9 V, about 1.0 V, about 1.1 V, about 1.2 V, about 1.3 V, about 1.4 V, about 1.5 V, about 1.6 V, about 1.7 V, about 1.8 V, about 1.9 V, about 2.0 V, about 2.1 V, about 2.2 V, about 2.3 V, about 2.4 V, about 2.5 V, about 2.6 V, about 2.7 V, about 2.8 V, about 2.9 V, about 3.0 V, about 3.1 V, about 3.2 V, about 3.3 V, about 3.4 V, about 3.5 V, about 3.6 V, about 3.7 V, about 3.8 V, about 3.9 V, about 4.0 V, about 4.1 V, about 4.2 V, about 4.3 V, about 4.4 V, about 4.5 V, about 4.6 V, about 4.7 V, about 4.8 V, about 4.9 V, about 5.0 V, about 5.1 V, about 5.2 V, about 5.3 V, about 5.4 V, about 5.5 V, about 5.6 V, about 5.7 V, about 5.8 V, about 5.9 V, about 6.0 V, or the like.

In embodiments, systems and devices disclosed herein can produce a low level electric current of between for example about 1 and about 200 micro-amperes, between about 10 and about 190 micro-amperes, between about 20 and about 180 micro-amperes, between about 30 and about 170 micro-amperes, between about 40 and about 160 micro-amperes, between about 50 and about 150 micro-amperes, between about 60 and about 140 micro-amperes, between about 70 and about 130 micro-amperes, between about 80 and about 120 micro-amperes, between about 90 and about 100 micro-amperes, or the like.

In embodiments, systems and devices disclosed herein can produce a low level electric current of between for example about 1 and about 400 micro-amperes, between about 20 and about 380 micro-amperes, between about 40 and about 360 micro-amperes, between about 60 and about 340 micro-amperes, between about 80 and about 320 micro-amperes, between about 100 and about 300 micro-amperes, between about 120 and about 280 micro-amperes, between about 140 and about 260 micro-amperes, between about 160 and about 240 micro-amperes, between about 180 and about 220 micro-amperes, or the like.

In embodiments, systems and devices disclosed herein can produce a low level electric current of between for example about 1 micro-ampere and about 1 milli-ampere, between about 50 and about 800 micro-amperes, between about 200 and about 600 micro-amperes, between about 400 and about 500 micro-amperes, or the like.

In embodiments, systems and devices disclosed herein can produce a low level electric current of about 10 micro-amperes, about 20 micro-amperes, about 30 micro-amperes, about 40 micro-amperes, about 50 micro-amperes, about 60 micro-amperes, about 70 micro-amperes, about 80 micro-amperes, about 90 micro-amperes, about 100 micro-amperes, about 110 micro-amperes, about 120 micro-amperes, about 130 micro-amperes, about 140 micro-amperes, about 150 micro-amperes, about 160 micro-amperes, about 170 micro-amperes, about 180 micro-amperes, about 190 micro-amperes, about 200 micro-amperes, about 210 micro-amperes, about 220 micro-amperes, about 240 micro-amperes, about 260 micro-amperes, about 280 micro-amperes, about 300 micro-amperes, about 320 micro-amperes, about 340 micro-amperes, about 360 micro-amperes, about 380 micro-amperes, about 400 micro-amperes, about 450 micro-amperes, about 500 micro-amperes, about 550 micro-amperes, about 600 micro-amperes, about 650 micro-amperes, about 700 micro-amperes, about 750 micro-amperes, about 800 micro-amperes, about 850 micro-amperes, about 900 micro-amperes, about 950 micro-amperes, about 1 milli-ampere, or the like.

In embodiments, the disclosed systems and devices can produce a low level electric current of not more than 10 micro-amperes, or not more than about 20 micro-amperes, not more than about 30 micro-amperes, not more than about 40 micro-amperes, not more than about 50 micro-amperes, not more than about 60 micro-amperes, not more than about 70 micro-amperes, not more than about 80 micro-amperes, not more than about 90 micro-amperes, not more than about 100 micro-amperes, not more than about 110 micro-amperes, not more than about 120 micro-amperes, not more than about 130 micro-amperes, not more than about 140 micro-amperes, not more than about 150 micro-amperes, not more than about 160 micro-amperes, not more than about 170 micro-amperes, not more than about 180 micro-amperes, not more than about 190 micro-amperes, not more than about 200 micro-amperes, not more than about 210 micro-amperes, not more than about 220 micro-amperes, not more than about 230 micro-amperes, not more than about 240 micro-amperes, not more than about 250 micro-amperes, not more than about 260 micro-amperes, not more than about 270 micro-amperes, not more than about 280 micro-amperes, not more than about 290 micro-amperes, not more than about 300 micro-amperes, not more than about 310 micro-amperes, not more than about 320 micro-amperes, not more than about 340 micro-amperes, not more than about 360 micro-amperes, not more than about 380 micro-amperes, not more than about 400 micro-amperes, not more than about 420 micro-amperes, not more than about 440 micro-amperes, not more than about 460 micro-amperes, not more than about 480 micro-amperes, not more than about 500 micro-amperes, not more than about 520 micro-amperes, not more than about 540 micro-amperes, not more than about 560 micro-amperes, not more than about 580 micro-amperes, not more than about 600 micro-amperes, not more than about 620 micro-amperes, not more than about 640 micro-amperes, not more than about 660 micro-amperes, not more than about 680 micro-amperes, not more than about 700 micro-amperes, not more than about 720 micro-amperes, not more than about 740 micro-amperes, not more than about 760 micro-amperes, not more than about 780 micro-amperes, not more than about 800 micro-amperes, not more than about 820 micro-amperes, not more than about 840 micro-amperes, not more than about 860 micro-amperes, not more than about 880 micro-amperes, not more than about 900 micro-amperes, not more than about 920 micro-amperes, not more than about 940 micro-amperes, not more than about 960 micro-amperes, not more than about 980 micro-amperes, or the like.

In embodiments, systems and devices disclosed herein can produce a low level electric current of not less than 10 micro-amperes, not less than 20 micro-amperes, not less than 30 micro-amperes, not less than 40 micro-amperes, not less than 50 micro-amperes, not less than 60 micro-amperes, not less than 70 micro-amperes, not less than 80 micro-amperes, not less than 90 micro-amperes, not less than 100 micro-amperes, not less than 110 micro-amperes, not less than 120 micro-amperes, not less than 130 micro-amperes, not less than 140 micro-amperes, not less than 150 micro-amperes, not less than 160 micro-amperes, not less than 170 micro-amperes, not less than 180 micro-amperes, not less than 190 micro-amperes, not less than 200 micro-amperes, not less than 210 micro-amperes, not less than 220 micro-amperes, not less than 230 micro-amperes, not less than 240 micro-amperes, not less than 250 micro-amperes, not less than 260 micro-amperes, not less than 270 micro-amperes, not less than 280 micro-amperes, not less than 290 micro-amperes, not less than 300 micro-amperes, not less than 310 micro-amperes, not less than 320 micro-amperes, not less than 330 micro-amperes, not less than 340 micro-amperes, not less than 350 micro-amperes, not less than 360 micro-amperes, not less than 370 micro-amperes, not less than 380 micro-amperes, not less than 390 micro-amperes, not less than 400 micro-amperes, not less than about 420 micro-amperes, not less than about 440 micro-amperes, not less than about 460 micro-amperes, not less than about 480 micro-amperes, not less than about 500 micro-amperes, not less than about 520 micro-amperes, not less than about 540 micro-amperes, not less than about 560 micro-amperes, not less than about 580 micro-amperes, not less than about 600 micro-amperes, not less than about 620 micro-amperes, not less than about 640 micro-amperes, not less than about 660 micro-amperes, not less than about 680 micro-amperes, not less than about 700 micro-amperes, not less than about 720 micro-amperes, not less than about 740 micro-amperes, not less than about 760 micro-amperes, not less than about 780 micro-amperes, not less than about 800 micro-amperes, not less than about 820 micro-amperes, not less than about 840 micro-amperes, not less than about 860 micro-amperes, not less than about 880 micro-amperes, not less than about 900 micro-amperes, not less than about 920 micro-amperes, not less than about 940 micro-amperes, not less than about 960 micro-amperes, not less than about 980 micro-amperes, or the like.

In embodiments the electric field can be extended, for example through the use of a hydrogel. A hydrogel is a network of polymer chains that are hydrophilic. Hydrogels are highly absorbent natural or synthetic polymeric networks. Hydrogels can be configured to contain a high percentage of water (e.g. they can contain over 90% water). Hydrogels can possess a degree of flexibility very similar to natural tissue, due to their significant water content. A hydrogel can be configured in a variety of viscosities. Viscosity is a measurement of a fluid or material's resistance to gradual deformation by shear stress or tensile stress. In embodiments the electrical field can be extended through a semi-liquid hydrogel with a low viscosity such an ointment or a cellular culture medium. In other embodiments the electrical field can be extended through a solid hydrogel with a high viscosity such as a Petri dish, clothing, or material used to manufacture a prosthetic. In general, the hydrogel described herein may be configured to a viscosity of between about 0.5 Pas and greater than about $10^{12}$ Pa·s. In embodiments the viscosity of a hydrogel can be, for example, between 0.5 and $10^{12}$ Pa·s, between 1 Pa·s and $10^6$ Pa·s, between 5 and $10^3$ Pa·s, between 10 and 100 Pas, between 15 and 90 Pa·s, between 20 and 80 Pas, between 25 and 70 Pas, between 30 and 60 Pas, or the like.

In embodiments the substrate can comprise a hydrogel.

In another embodiment, the reservoirs or dots are configured to be same specific gravity as the hydrophilic polymer base of a hydrogel. This embodiment allows the reservoirs or dots to be suspended in the hydrogel for a desired use without the reservoirs or dots being pulled to the bottom of the hydrogels due to other factors such as gravity. In particular, the reservoirs or dots will not settle and the hydrogel can be manufactured and stored for extended periods of times without altering the hydrogel's intended performance.

In certain embodiments that utilize a poly-cellulose binder, the binder itself can have a beneficial effect such as reducing the local concentration of matrix metallo-proteases through an iontophoretic process that drives the cellulose into the surrounding tissue. This process can be used to electronically drive other components such as drugs into the surrounding tissue.

The binder can comprise any biocompatible liquid material that can be mixed with a conductive element (preferably metallic crystals of silver or zinc) to create a conductive solution which can be applied to a substrate. One suitable binder is a solvent reducible polymer, such as the polyacrylic non-toxic silk-screen ink manufactured by COLORCON® Inc., a division of Berwind Pharmaceutical Services, Inc. (see COLORCON® NO-TOX® product line, part number NT28). In an embodiment the binder is mixed with high purity (at least 99.99%, in an embodiment) metallic silver crystals to make the silver conductive solution. The silver crystals, which can be made by grinding silver into a powder, are preferably smaller than 100 microns in size or about as fine as flour. In an embodiment, the size of the crystals is about 325 mesh, which is typically about 40 microns in size or a little smaller. The binder is separately mixed with high purity (at least 99.99%, in an embodiment) metallic zinc powder which has also preferably been sifted through standard 325 mesh screen, to make the zinc conductive solution.

Other powders of metal can be used to make other conductive metal solutions in the same way as described in other embodiments.

When COLORCON® polyacrylic ink is used as the binder, about 10 to 40 percent of the mixture should be metal for a long term bandage (for example, one that stays on for about 10 days). For example, for a long term LLEC or LLEF system the percent of the mixture that should be metal can be 8 percent, or 10 percent, 12 percent, 14 percent, 16 percent, 18 percent, 20 percent, 22 percent, 24 percent, 26 percent, 28 percent, 30 percent, 32 percent, 34 percent, 36 percent, 38 percent, 40 percent, 42 percent, 44 percent, 46 percent, 48 percent, 50 percent, or the like.

If the same binder is used, but the percentage of the mixture that is metal is increased to 60 percent or higher, a typical system will be effective for longer. For example, for a longer term device, the percent of the mixture that should be metal can be 40 percent, or 42 percent, 44 percent, 46 percent, 48 percent, 50 percent, 52 percent, 54 percent, 56 percent, 58 percent, 60 percent, 62 percent, 64 percent, 66 percent, 68 percent, 70 percent, 72 percent, 74 percent, 76 percent, 78 percent, 80 percent, 82 percent, 84 percent, 86 percent, 88 percent, 90 percent, or the like.

For systems comprising a pliable substrate it can be desired to decrease the percentage of metal down to 5 percent or less, or to use a binder that causes the crystals to be more deeply embedded, so that the primary surface will be antimicrobial for a very long period of time and will not wear prematurely. Other binders can dissolve or otherwise break down faster or slower than a polyacrylic ink, so adjustments can be made to achieve the desired rate of spontaneous reactions from the voltaic cells.

Figure 2:
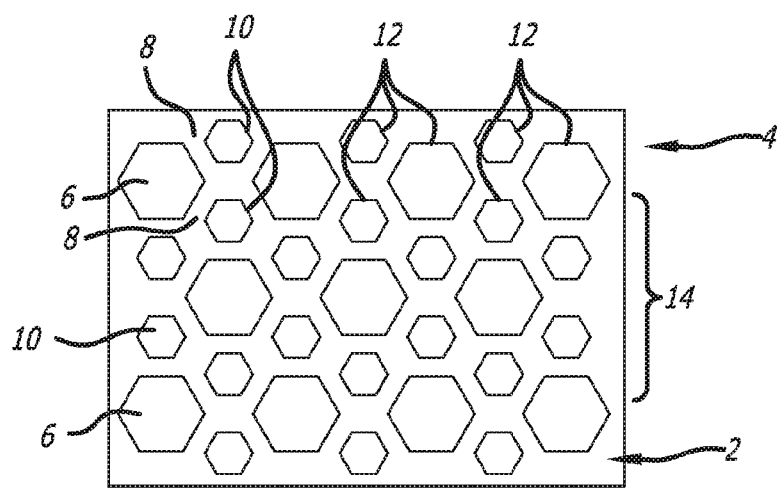
FIG. 2 depicts a detailed plan view of a substrate layer microcell pattern of applied electrical conductors according to one or more embodiments.

To maximize the number of voltaic cells, in various embodiments, a pattern of alternating silver masses (e.g., 6 as shown in FIG. 1) or electrodes or reservoirs and zinc masses (e.g., 10 as shown in FIG. 1) or electrodes or reservoirs can create an array of electrical currents. A basic embodiment, shown in FIG. 1, has each mass of silver randomly spaced from masses of zinc, and has each mass of zinc randomly spaced from masses of silver, according to an embodiment. In another embodiment, mass of silver can be equally spaced from masses of zinc, and has each mass of zinc equally spaced from masses of silver. That is, the electrodes or reservoirs or dots can either be a uniform pattern, a random pattern, or a combination of the like. The first electrode 6 is separated from the second electrode 10. The designs of first electrode 6 and second electrode 10 are simply round dots, and in an embodiment, are repeated throughout the hydrogel. For an exemplary device comprising silver and zinc, each silver design preferably has about twice as much mass as each zinc design, in an embodiment. For the embodiment in FIG. 1, the silver designs are most preferably about a millimeter from each of the closest four zinc designs, and vice-versa. The resulting pattern of dissimilar metal masses defines an array of voltaic cells when introduced to an electrolytic solution. To maximize the density of electrical current over a primary surface the pattern of FIG. 2 can be used. The first electrode 6 in FIG. 2 is a large hexagonally shaped dot, and the second electrode 10 is a pair of smaller hexagonally shaped dots that are spaced from each other. The spacing 8 that is between the first electrode 6 and the second electrode 10 maintains a relatively consistent distance between adjacent sides of the designs. Numerous repetitions 12 of the designs result in a pattern 14 that can be described as at least one of the first design being surrounded by six hexagonally shaped dots of the second design.

Figure 3:
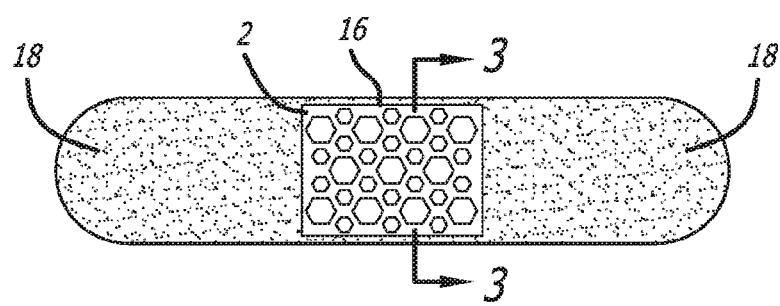
FIG. 3 depicts an embodiment using the applied pattern of FIG. 2 according to one or more embodiments.
Figure 4:
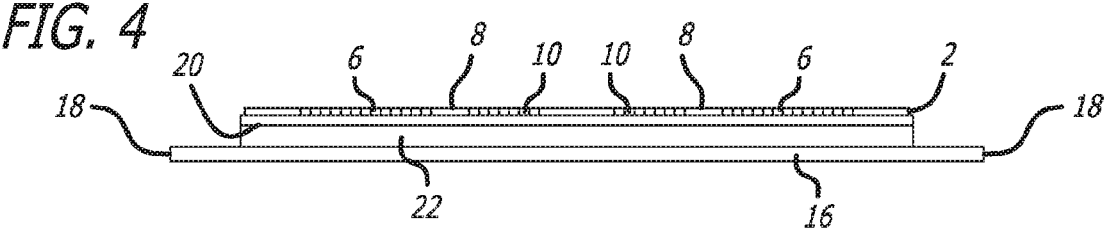
FIG. 4 depicts a cross-section of the embodiment of FIG. 3 through line 3-3.

FIGS. 3 and 4 show how the pattern of FIG. 2 can be used to make an embodiment disclosed herein. The pattern shown in detail in FIG. 2 is applied to the primary surface 2 of an embodiment. The back 20 of the printed material is fixed to a substrate layer 22. This layer is adhesively fixed to a pliable layer 16.

Figure 5:
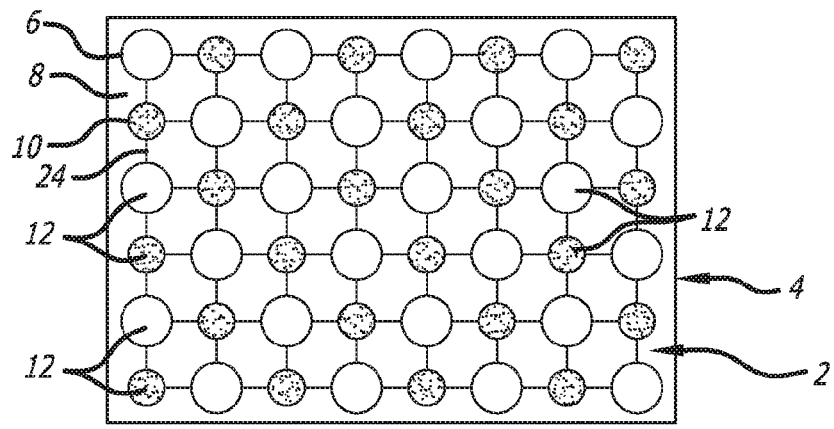
FIG. 5 depicts a detailed plan view of an alternate substrate embodiment disclosed herein which includes fine lines of conductive metal solution connecting electrodes.

FIG. 5 shows an additional feature that can initiate the flow of current in a poor electrolytic solution. A fine line 24 is printed using one of the conductive metal solutions along a current path of each voltaic cell. The fine line will initially have a direct reaction but will be depleted until the distance between the electrodes increases to where maximum voltage is realized. The initial current produced is intended to help control edema so that the iontophoresis system will be effective. If the electrolytic solution is highly conductive when the system is initially applied the fine line can be quickly depleted and the device will function as though the fine line had never existed.

Figure 6:
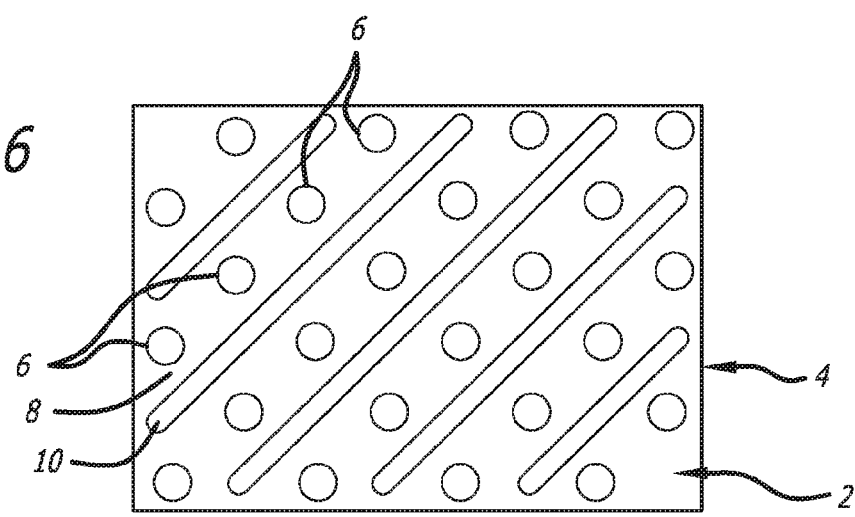
FIG. 6 depicts a detailed plan view of another alternate substrate embodiment having a line pattern and dot pattern.
Figure 7:
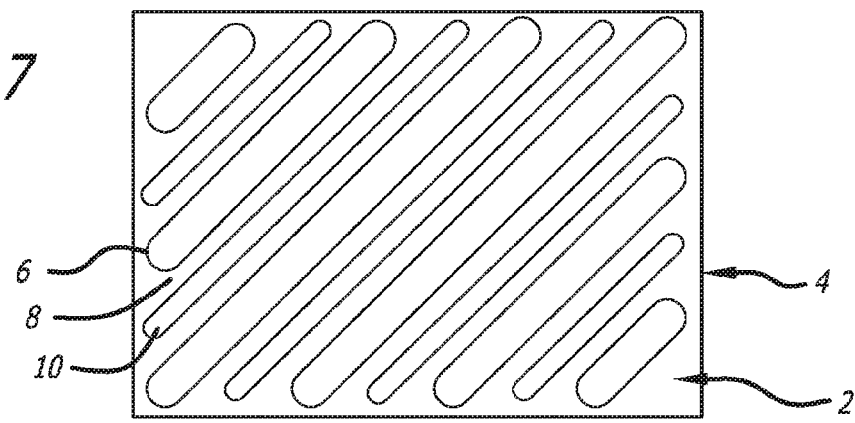
FIG. 7 depicts a detailed plan view of another alternate substrate embodiment having two line patterns.

FIGS. 6 and 7 show alternative patterns that use at least one line design. The first electrode 6 of FIG. 6 is a round dot similar to the first design used in FIG. 1. The second electrode 10 of FIG. 6 is a line. When the designs are repeated, they define a pattern of parallel lines that are separated by numerous spaced dots. FIG. 7 uses only line designs. The first electrode 6 can be thicker or wider than the second electrode 10 if the oxidation-reduction reaction requires more metal from the first conductive element (mixed into the first design's conductive metal solution) than the second conductive element (mixed into the second design's conductive metal solution). The lines can be dashed. Another pattern can be silver grid lines that have zinc masses in the center of each of the cells of the grid. The pattern can be letters printed from alternating conductive materials so that a message can be printed onto the primary surface-perhaps a brand name or identifying information such as patient blood type.

Figure 8:
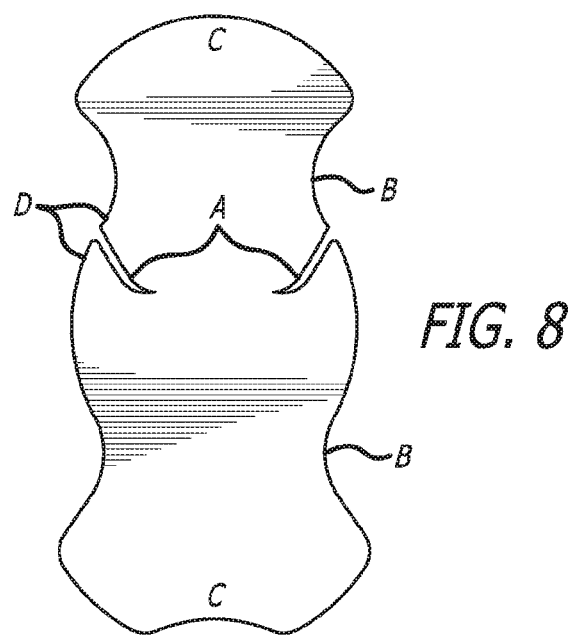
FIG. 8 depicts an embodiment for use on the knee joint.

FIG. 8 shows an embodiment for treatment of the knee. Bend relief cuts (A) provide for universal conformability while improving joint mobility. Larger radius cuts (B) reduce wrinkling in corners. Convex (and/or concave) curvature (C) provides for improved conformability around the shin or thigh. Edges (D) meet flush upon overlap for smooth aesthetic appearance, regardless the angle applied.

Figure 9:
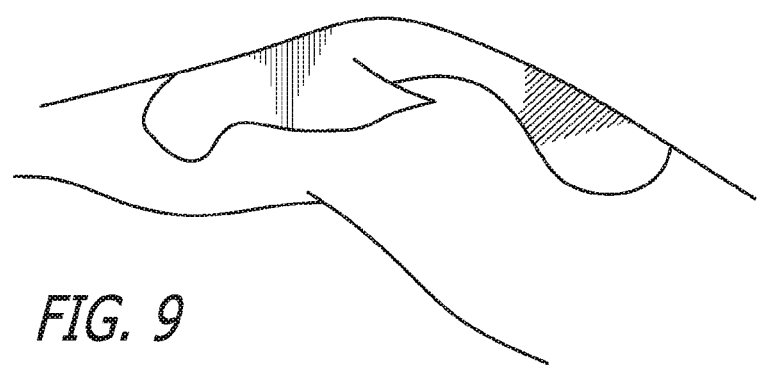
FIG. 9 depicts the embodiment for use on the knee joint as it is applied to a patient.

FIG. 9 shows an embodiment for treatment of the knee as it is applied to a subject.

Figure 10:
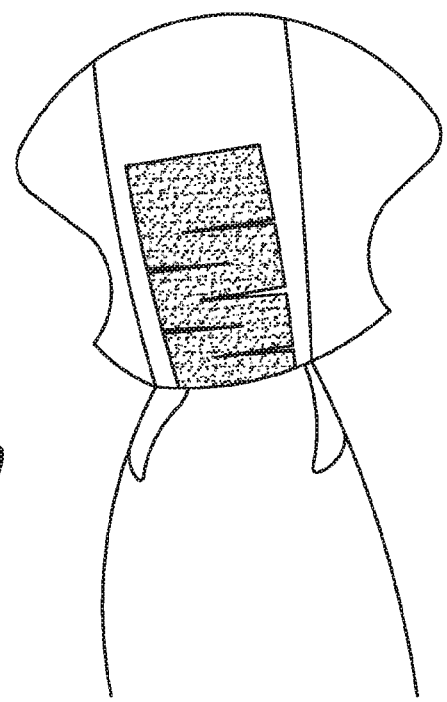
FIG. 10 depicts the treatment side of a disclosed embodiment showing the substrate microcell pattern.

FIG. 10 shows the contact (treatment) side of a disclosed device, comprising a microcell pattern as shown in FIG. 1. The adhesive layer extends beyond the perimeter of the microcell pattern, thus securing the device to the treatment area.

Figure 11:
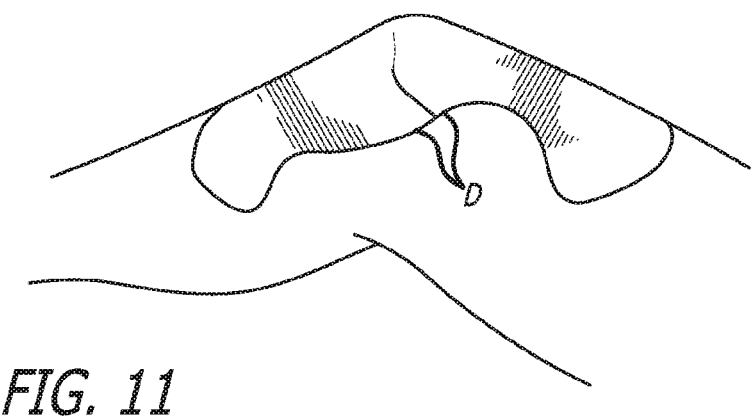
FIG. 11 depicts an embodiment for use on the knee joint after it is applied to a patient.

FIG. 11 shows an embodiment for treatment of the knee after it is applied to a subject. Edges (D) meet flush upon overlap for smooth aesthetic appearance, regardless the angle applied.

Figure 12A:
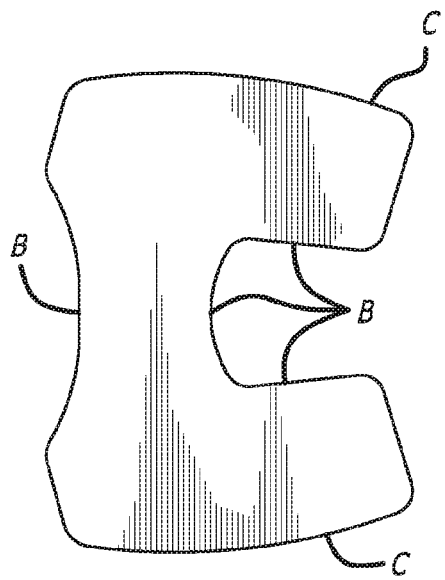
FIGS. 12A-12B depict an embodiment for use on the elbow joint.
Figure 12B:
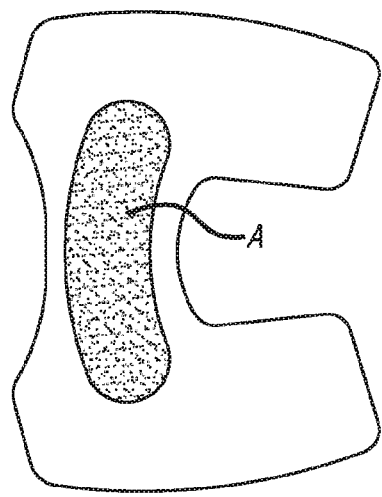

FIGS. 12A-12B show an embodiment for treatment of the elbow. Microcell substrate (A) provides an LLEC or LLEF. Elongated perimeter (B) conforms around the joint to allow for proper articulation. Flanges (C) wrap around the forearm and bicep for additional adhesion. The embodiment is symmetrical so that it can be used with either a medial or lateral incision, such as performed during corrective surgery for lateral epicondylitis.

Figure 13A:
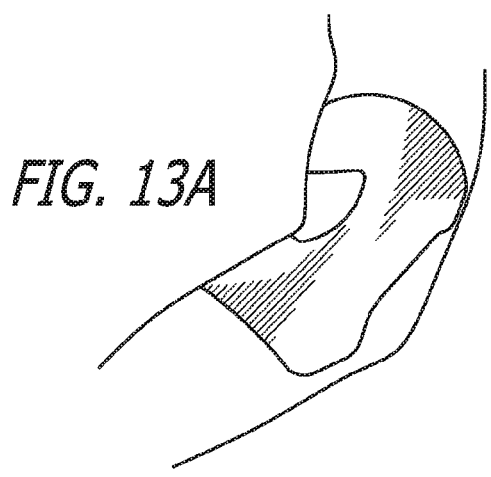
FIGS. 13A-13B depict an embodiment for use on the elbow joint (lateral side) after it is applied to a patient.
Figure 13B:
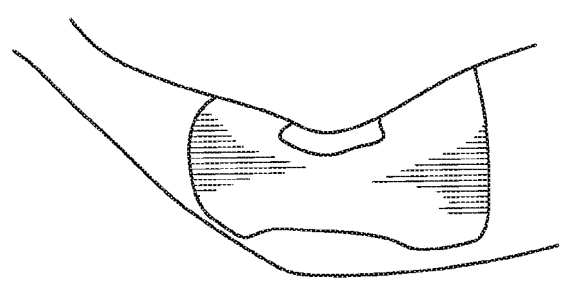

FIGS. 13A and 13B show an embodiment for treatment of a lateral injury or incision of the elbow after it is applied to a subject.

Figure 14A:
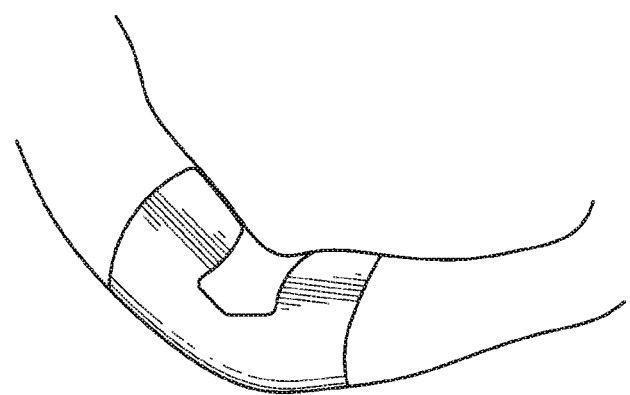
FIGS. 14A-14B depict an embodiment for use on the elbow joint (medial side) after it is applied to a patient.
Figure 14B:
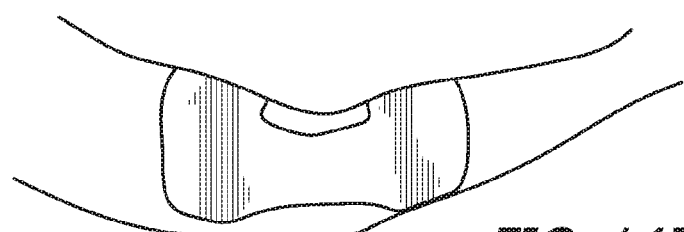

FIGS. 14A and 14B show an embodiment for treatment of a medial injury or incision of the elbow after it is applied to a subject.

Figures 15A, 15B:
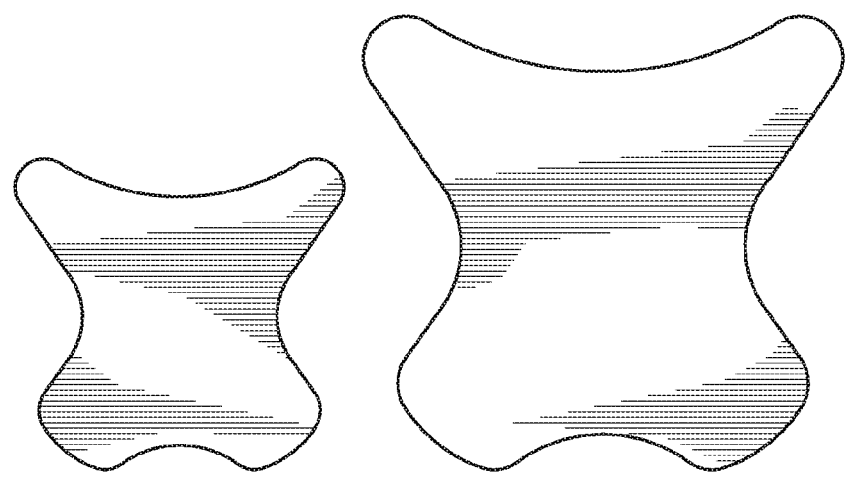
FIGS. 15A-15B depict a "universal" embodiment for use on multiple areas of the body.
Figure 16D:
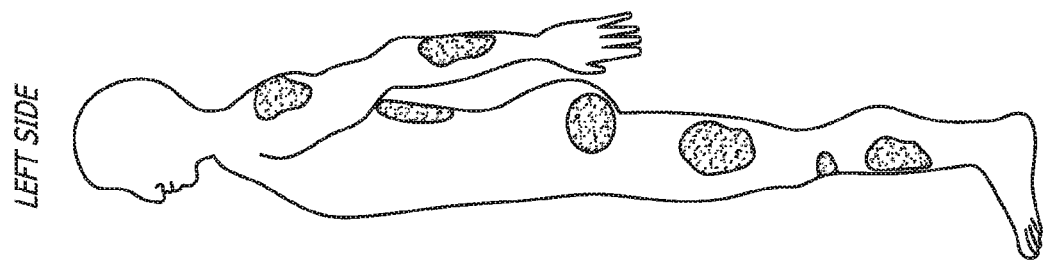
FIGS. 16A-16D depict prospective areas for treatment with the universal embodiment in FIG. 15.
Figure 16C:
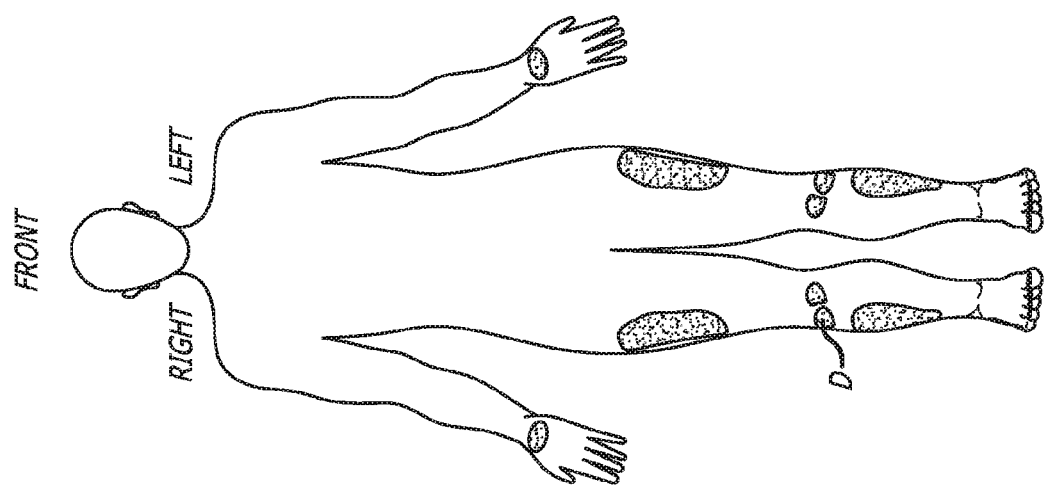
Figure 16B:
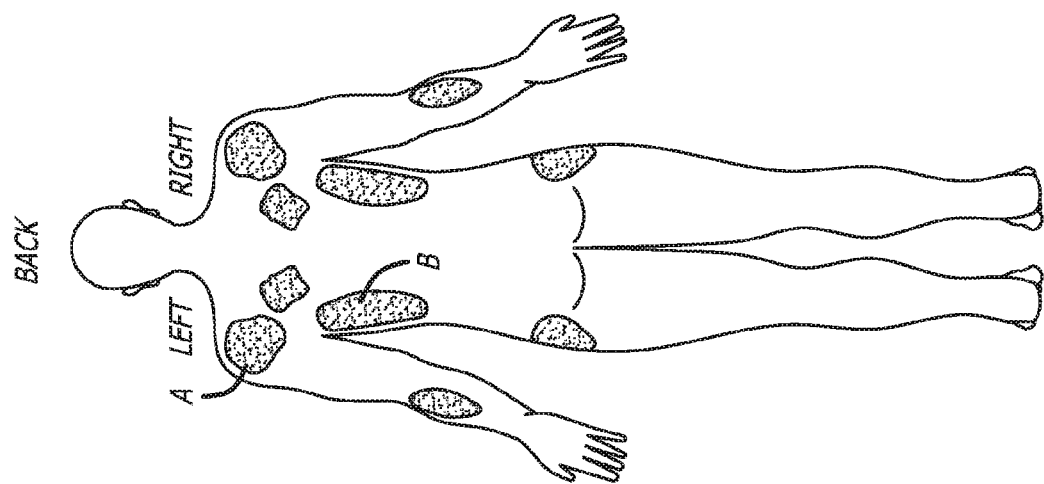
Figure 16A:
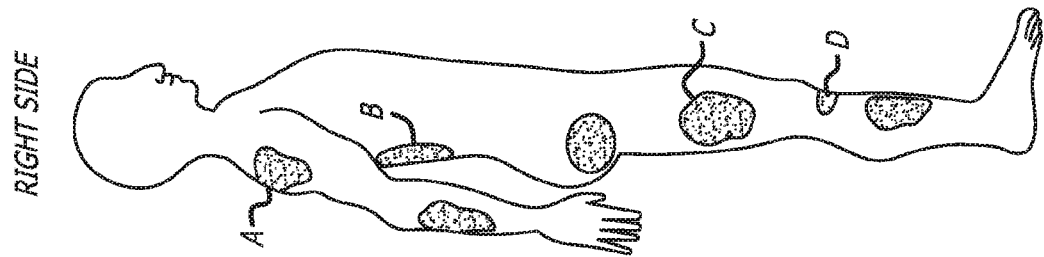
Figure 17C:
FIGS. 17A-17E depict a universal embodiment in use.
Figure 17E:
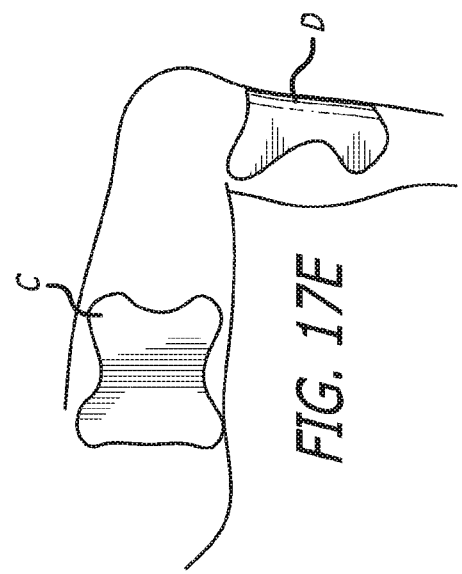
Figure 17B:
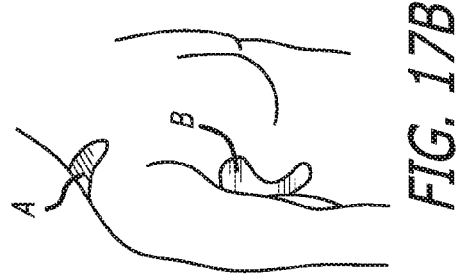
Figure 17A:
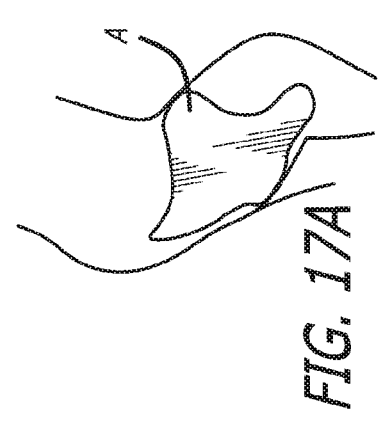
Figure 17D:
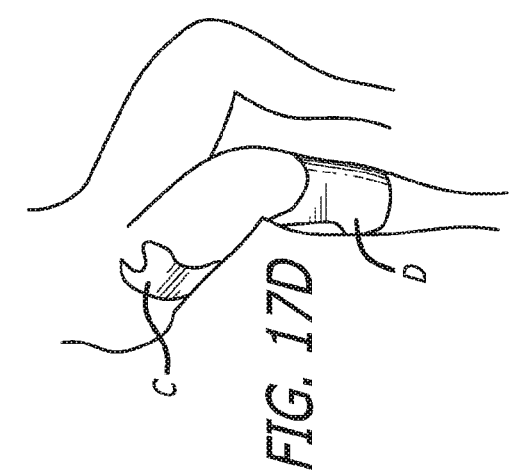

FIGS. 15A and 15B show a universal embodiment as disclosed herein. The design of the embodiment provides for compatibility with numerous areas of the body.

FIGS. 16A-16D show prospective treatment areas using a disclosed universal embodiment.

FIGS. 17A-17E depict the universal embodiment in use.

Figure 18:
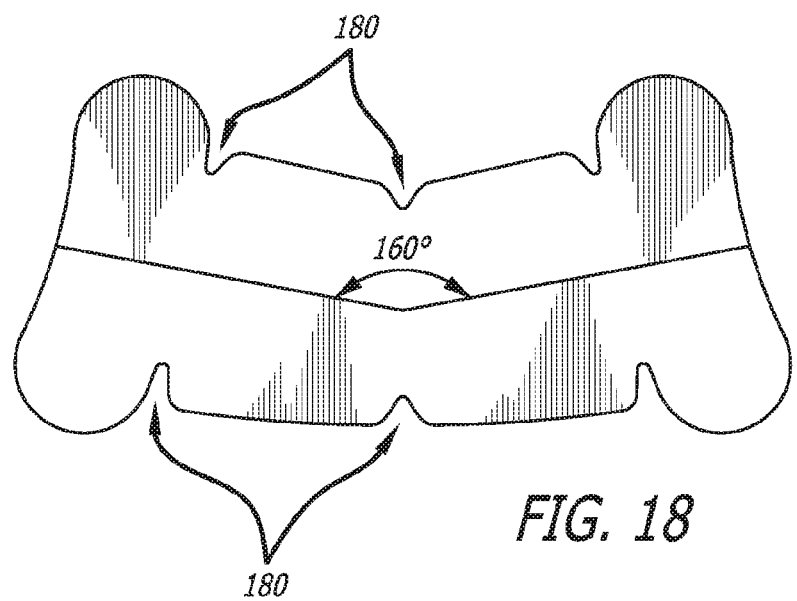
FIG. 18 depicts an embodiment for use on the knee, elbow or shoulder.

FIG. 18 depicts an embodiment for use on the elbow or shoulder. Stretch/bend relief areas 180 provide maximum range of motion without pulling the skin. The 160° angle conforms to elbow and shoulder contours, for example to cover a total shoulder arthroplasty incision. This angle can, in various embodiments, be 90, 100, 110, 120, 130, 140, 150, 160, 170, 180, or the like.

Figure 19:
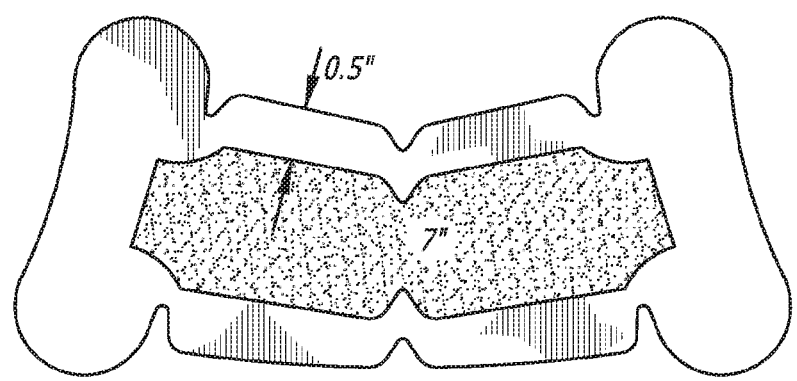
FIG. 19 depicts the treatment side of an embodiment for use on the knee, elbow or shoulder.

FIG. 19 shows the treatment side of the embodiment of FIG. 18. The embodiment provides a 7" long microcell array to cover the majority of incision lengths and shapes, while the 0.5" adhesive border surrounding the microcell array secures the bandage.

Figure 20A:
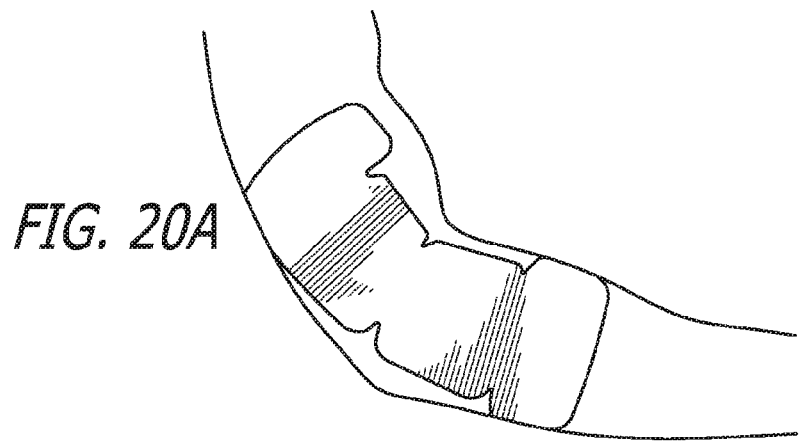
FIGS. 20A-20C depict the embodiments of FIGS. 18 and 19 as applied to a patient's elbow.

FIGS. 20A-20O depict the embodiments of FIGS. 18 and 19 as applied to a patient.

Because the spontaneous oxidation-reduction reaction of silver and zinc uses a ratio of approximately two silver to one zinc, the silver design can contain about twice as much mass as the zinc design in an embodiment. At a spacing of about 1 mm between the closest dissimilar metals (closest edge to closest edge) each voltaic cell that contacts a conductive fluid such as a cosmetic cream can create approximately 1 volt of potential that will penetrate substantially through its surrounding surfaces. Closer spacing of the dots can reduce the strength of the electric field and the current will not penetrate as deeply. Therefore, spacing between the closest conductive materials can be, for example, 1 µm, 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 36 µm, 37 µm, 38 µm, 39 µm, 40 µm, 41 µm, 42 µm, 43 µm, 44 µm, 45 µm, 46 µm, 47 µm, 48 µm, 49 µm, 50 µm, 51 µm, 52 µm, 53 µm, 54 µm, 55 µm, 56 µm, 57 µm, 58 µm, 59 µm, 60 µm, 61 µm, 62 µm, 63 µm, 64 µm, 65 µm, 66 µm, 67 µm, 68 µm, 69 µm, 70 µm, 71 µm, 72 µm, 73 µm, 74 µm, 75 µm, 76 µm, 77 µm, 78 µm, 79 µm, 80 µm, 81 µm, 82 µm, 83 µm, 84 µm, 85 µm, 86 µm, 87 µm, 88 µm, 89 µm, 90 µm, 91 µm, 92 µm, 93 µm, 94 µm, 95 µm, 96 µm, 97 µm, 98 µm, 99 µm, 0.1 mm, or 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, or the like.

In certain embodiments the spacing between the closest conductive materials can be not more than 1 µm, or not more than 2 µm, or not more than 3 µm, or not more than 4 µm, or not more than 5, or not more than 6 µm, or not more than 7 µm, or not more than 8 µm, or not more than 9 µm, or not more than 10 µm, or not more than 11 µm, or not more than 12 µm, or not more than 13 µm, or not more than 14 µm, or not more than 15 µm, or not more than 16, or µm not more than 17 or µm, or not more than 18 µm, or not more than 19, or µm not more than 20, or µm not more than 21, or µm not more than 22 µm, or not more than 23 or µm, or not more than 24 µm, or not more than 25 µm, or not more than 26 µm, or not more than 27 µm, or not more than 28 µm, or not more than 29 µm, or not more than 30 µm, or not more than 31 µm, or not more than 32 µm, or not more than 33 µm, or not more than 34 µm, or not more than 35 µm, or not more than 36 µm, or not more than 37 µm, or not more than 38 µm, or not more than 39 µm, or not more than 40 µm, or not more than 41 µm, or not more than 42 µm, or not more than 43 µm, or not more than 44 µm, or not more than 45 µm, or not more than 46 µm, or not more than 47 µm, or not more than 48 µm, or not more than 49 µm, or not more than 50 µm, or not more than 51 µm, or not more than 52 µm, or not more than 53 µm, or not more than 54 µm, or not more than 55 µm, or not more than 56 µm, or not more than 57 µm, or not more than 58 µm, or not more than 59 µm, or not more than 60 µm, or not more than 61 µm, or not more than 62 µm, or not more than 63 µm, or not more than 64 µm, or not more than 65 µm, or not more than 66 µm, or not more than 67 µm not more than 68 µm not more than 69 µm, or not more than 70 µm, or not more than 71 µm, or not more than 72 µm, or not more than 73 µm, or not more than 74 µm, or not more than 75 µm, or not more than 76 µm, or not more than 77 µm, or not more than 78 µm, or not more than 79 µm, or not more than 80 µm, or not more than 81 µm, or not more than 82 µm, or not more than 83 µm, or not more than 84 µm, or not more than 85 µm, or not more than 86 µm, or not more than 87 µm, or not more than 88 µm, or not more than 89 µm, or not more than 90 µm, or not more than 91 µm, or not more than 92 µm, or not more than 93 µm, or not more than 94 µm, or not more than 95 µm, or not more than 96 µm, or not more than 97 µm, or not more than 98 µm, or not more than 99 µm, or not more than not more than 0.1 mm, not more than 0.2 mm, not more than 0.3 mm, not more than 0.4 mm, not more than 0.5 mm, not more than 0.6 mm, not more than 0.7 mm, not more than 0.8 mm, not more than 0.9 mm, not more than 1 mm, not more than 1.1 mm, not more than 1.2 mm, not more than 1.3 mm, not more than 1.4 mm, not more than 1.5 mm, not more than 1.6 mm, not more than 1.7 mm, not more than 1.8 mm, not more than 1.9 mm, not more than 2 mm, not more than 2.1 mm, not more than 2.2 mm, not more than 2.3 mm, not more than 2.4 mm, not more than 2.5 mm, not more than 2.6 mm, not more than 2.7 mm, not more than 2.8 mm, not more than 2.9 mm, not more than 3 mm, not more than 3.1 mm, not more than 3.2 mm, not more than 3.3 mm, not more than 3.4 mm, not more than 3.5 mm, not more than 3.6 mm, not more than 3.7 mm, not more than 3.8 mm, not more than 3.9 mm, not more than 4 mm, not more than 4.1 mm, not more than 4.2 mm, not more than 4.3 mm, not more than 4.4 mm, not more than 4.5 mm, not more than 4.6 mm, not more than 4.7 mm, not more than 4.8 mm, not more than 4.9 mm, not more than 5 mm, not more than 5.1 mm, not more than 5.2 mm, not more than 5.3 mm, not more than 5.4 mm, not more than 5.5 mm, not more than 5.6 mm, not more than 5.7 mm, not more than 5.8 mm, not more than 5.9 mm, not more than 6 mm, or the like.

In certain embodiments spacing between the closest conductive materials can be not less than 1 µm, or not less than 2 µm, or not less than 3 µm, or not less than 4 µm, or not less than 5 µm, or not less than 6 µm, or not less than 7 µm, or not less than 8 µm, or not less than 9 µm, or not less than 10 µm, or not less than 11 µm, or not less than 12 µm, or not less than 13 µm, or not less than 14 µm, or not less than 15 µm, or not less than 16 µm, or not less than 17 µm, or not less than 18 µm, or not less than 19 µm, or not less than 20 µm, or not less than 21 µm, or not less than 22 µm, or not less than 23 µm, or not less than 24 µm, or not less than 25 µm, or not less than 26 µm, or not less than 27 µm, or not less than 28 µm, or not less than 29 µm, or not less than 30 µm, or not less than 31 µm, or not less than 32 µm, or not less than 33 µm, or not less than 34 µm, or not less than 35 µm, or not less than 36 µm, or not less than 37 µm, or not less than 38 µm, or not less than 39 µm, or not less than 40 µm, or not less than 41 µm, or not less than 42 µm, or not less than 43 µm, or not less than 44 µm, or not less than 45 µm, or not less than 46 µm, or not less than 47 µm, or not less than 48 µm, or not less than 49 µm, or not less than 50 µm, or not less than 51 µm, or not less than 52 µm, or not less than 53 µm, or not less than 54 µm, or not less than 55 µm, or not less than 56 µm, or not less than 57 µm, or not less than 58 µm, or not less than 59 µm, or not less than 60 µm, or not less than 61 µm, or not less than 62 µm, or not less than 63 µm, or not less than 64 µm, or not less than 65 µm, or not less than 66 µm, or not less than 67 µm, or not less than 68 µm, or not less than 69 µm, or not less than 70 µm, or not less than 71 µm, or not less than 72 µm, or not less than 73 µm, or not less than 74 µm, or not less than 75 µm, or not less than 76 µm, or not less than 77 µm, or not less than 78 µm, or not less than 79 µm, or not less than 80 µm, or not less than 81 µm, or not less than 82 µm, or not less than 83 µm, or not less than 84 µm, or not less than 85 µm, or not less than 86 µm, or not less than 87 µm, or not less than 88 µm, or not less than 89 µm, or not less than 90 µm, or not less than 91 µm, or not less than 92 µm, or not less than 93 µm, or not less than 94 µm, or not less than 95 µm, or not less than 96 µm, or not less than 97 µm, or not less than 98 µm, or not less than 99 µm, or not less than 0.1 mm, not less than 0.2 mm, not less than 0.3 mm, not less than 0.4 mm, not less than 0.5 mm, not less than 0.6 mm, not less than 0.7 mm, not less than 0.8 mm, not less than 0.9 mm, not less than 1 mm, not less than 1.1 mm, not less than 1.2 mm, not less than 1.3 mm, not less than 1.4 mm, not less than 1.5 mm, not less than 1.6 mm, not less than 1.7 mm, not less than 1.8 mm, not less than 1.9 mm, not less than 2 mm, not less than 2.1 mm, not less than 2.2 mm, not less than 2.3 mm, not less than 2.4 mm, not less than 2.5 mm, not less than 2.6 mm, not less than 2.7 mm, not less than 2.8 mm, not less than 2.9 mm, not less than 3 mm, not less than 3.1 mm, not less than 3.2 mm, not less than 3.3 mm, not less than 3.4 mm, not less than 3.5 mm, not less than 3.6 mm, not less than 3.7 mm, not less than 3.8 mm, not less than 3.9 mm, not less than 4 mm, not less than 4.1 mm, not less than 4.2 mm, not less than 4.3 mm, not less than 4.4 mm, not less than 4.5 mm, not less than 4.6 mm, not less than 4.7 mm, not less than 4.8 mm, not less than 4.9 mm, not less than 5 mm, not less than 5.1 mm, not less than 5.2 mm, not less than 5.3 mm, not less than 5.4 mm, not less than 5.5 mm, not less than 5.6 mm, not less than 5.7 mm, not less than 5.8 mm, not less than 5.9 mm, not less than 6 mm, or the like.

Embodiments comprise systems and devices comprising a hydrophilic polymer base and a first electrode design formed from a first conductive liquid that comprises a mixture of a polymer and a first element, the first conductive liquid being applied into a position of contact with the primary surface, the first element comprising a metal species, and the first electrode design comprising at least one dot or reservoir, wherein selective ones of the at least one dot or reservoir have approximately a 1.5 µm+/−1 µm mean diameter; a second electrode design formed from a second conductive liquid that comprises a mixture of a polymer and a second element, the second element comprising a different metal species than the first element, the second conductive liquid being printed into a position of contact with the primary surface, and the second electrode design comprising at least one other dot or reservoir, wherein selective ones of the at least one other dot or reservoir have approximately a 2 µm+/−2 µm mean diameter; a spacing on the primary surface that is between the first electrode design and the second electrode design such that the first electrode design does not physically contact the second electrode design, wherein the spacing is approximately 1.5 µm+/−1 µm, and at least one repetition of the first electrode design and the second electrode design, the at least one repetition of the first electrode design being substantially adjacent the second electrode design, wherein the at least one repetition of the first electrode design and the second electrode design, in conjunction with the spacing between the first electrode design and the second electrode design, defines at least one pattern of at least one voltaic cell for spontaneously generating at least one electrical current when introduced to an electrolytic solution. Therefore, electrodes, dots or reservoirs can have a mean diameter of 0.2 µm, 0.3 µm, 0.4 µm, 0.5 µm, 0.6 µm, 0.7 µm, 0.8 µm, 0.9 µm, 1.0 µm, 1.1 µm, 1.2 µm, 1.3 µm, 1.4 µm, 1.5 µm, 1.6 µm, 1.7 µm, 1.8 µm, 1.9 µm, 2.0 µm, 2.1 µm, 2.2 µm, 2.3 µm, 2.4 µm, 2.5 µm, 2.6 µm, 2.7 µm, 2.8 µm, 2.9 µm, 3.0 µm, 3.1 µm, 3.2 µm, 3.3 µm, 3.4 µm, 3.5 µm, 3.6 µm, 3.7 µm, 3.8 µm, 3.9 µm, 4.0 µm, 4.1 µm, 4.2 µm, 4.3 µm, 4.4 µm, 4.5 µm, 4.6 µm, 4.7 µm, 4.8 µm, 4.9 µm, 5.0 µm, or the like.

In further embodiments, electrodes, dots or reservoirs can have a mean diameter of not less than 0.2 µm, or not less than 0.3 µm, not less than 0.4 µm, not less than 0.5 µm, not less than 0.6 µm, not less than 0.7 µm, not less than 0.8 µm, not less than 0.9 µm, not less than 1.0 µm, not less than 1.1 µm, not less than 1.2 µm, not less than 1.3 µm, not less than 1.4 µm, not less than 1.5 µm, not less than 1.6 µm, not less than 1.7 µm, not less than 1.8 µm, not less than 1.9 µm, not less than 2.0 µm, not less than 2.1 µm, not less than 2.2 µm, not less than 2.3 µm, not less than 2.4 µm, not less than 2.5 µm, not less than 2.6 µm, not less than 2.7 µm, not less than 2.8 µm, not less than 2.9 µm, not less than 3.0 µm, not less than 3.1 µm, not less than 3.2 µm, not less than 3.3 µm, not less than 3.4 µm, not less than 3.5 µm, not less than 3.6 µm, not less than 3.7 µm, not less than 3.8 µm, not less than 3.9 µm, not less than 4.0 µm, not less than 4.1 µm, not less than 4.2 µm, not less than 4.3 µm, not less than 4.4 µm, not less than 4.5 µm, not less than 4.6 µm, not less than 4.7 µm, not less than 4.8 µm, not less than 4.9 µm, not less than 5.0 µm, or the like.

In further embodiments, electrodes, dots or reservoirs can have a mean diameter of not more than 0.2 µm, or not more than 0.3 µm, not more than 0.4 µm, not more than 0.5 µm, not more than 0.6 µm, not more than 0.7 µm, not more than 0.8 µm, not more than 0.9 µm, not more than 1.0 µm, not more than 1.1 µm, not more than 1.2 µm, not more than 1.3 µm, not more than 1.4 µm, not more than 1.5 µm, not more than 1.6 µm, not more than 1.7 µm, not more than 1.8 µm, not more than 1.9 µm, not more than 2.0 µm, not more than 2.1 µm, not more than 2.2 µm, not more than 2.3 µm, not more than 2.4 µm, not more than 2.5 µm, not more than 2.6 µm, not more than 2.7 µm, not more than 2.8 µm, not more than 2.9 µm, not more than 3.0 µm, not more than 3.1 µm, not more than 3.2 µm, not more than 3.3 µm, not more than 3.4 µm, not more than 3.5 µm, not more than 3.6 µm, not more than 3.7 µm, not more than 3.8 µm, not more than 3.9 µm, not more than 4.0 µm, not more than 4.1 µm, not more than 4.2 µm, not more than 4.3 µm, not more than 4.4 µm, not more than 4.5 µm, not more than 4.6 µm, not more than 4.7 µm, not more than 4.8 µm, not more than 4.9 µm, not more than 5.0 µm, or the like not exceeding 1 mm.

The material concentrations or quantities within and/or the relative sizes (e.g., dimensions or surface area) of the first and second reservoirs or dots or electrodes can be selected deliberately to achieve various characteristics of the systems' behavior. For example, the quantities of material within a first and second reservoir can be selected to provide an apparatus having an operational behavior that depletes at approximately a desired rate and/or that "dies" after an approximate period of time after activation. In an embodiment the one or more first reservoirs and the one or more second reservoirs are configured to sustain one or more currents for an approximate pre-determined period of time, after activation. It is to be understood that the amount of time that currents are sustained can depend on external conditions and factors (e.g., the quantity and type of activation material), and currents can occur intermittently depending on the presence or absence of activation material.

In various embodiments the difference of the standard potentials of the first and second reservoirs can be in a range from 0.05 V to approximately 5.0 V. For example, the standard potential can be 0.05 V, or 0.06 V, 0.07 V, 0.08 V, 0.09 V, 0.1 V, 0.2 V, 0.3 V, 0.4 V, 0.5 V, 0.6 V, 0.7 V, 0.8 V, 0.9 V, 1.0 V, 1.1 V, 1.2 V, 1.3 V, 1.4 V, 1.5 V, 1.6 V, 1.7 V, 1.8 V, 1.9 V, 2.0 V, 2.1 V, 2.2 V, 2.3 V, 2.4 V, 2.5 V, 2.6 V, 2.7 V, 2.8 V, 2.9 V, 3.0 V, 3.1 V, 3.2 V, 3.3 V, 3.4 V, 3.5 V, 3.6 V, 3.7 V, 3.8 V, 3.9 V, 4.0 V, 4.1 V, 4.2 V, 4.3 V, 4.4 V, 4.5 V, 4.6 V, 4.7 V, 4.8 V, 4.9 V, 5.0 V, or the like.

In a particular embodiment the difference of the standard potentials of the first and second reservoirs can be at least 0.05 V, or at least 0.06 V, at least 0.07 V, at least 0.08 V, at least 0.09 V, at least 0.1 V, at least 0.2 V, at least 0.3 V, at least 0.4 V, at least 0.5 V, at least 0.6 V, at least 0.7 V, at least 0.8 V, at least 0.9 V, at least 1.0 V, at least 1.1 V, at least 1.2 V, at least 1.3 V, at least 1.4 V, at least 1.5 V, at least 1.6 V, at least 1.7 V, at least 1.8 V, at least 1.9 V, at least 2.0 V, at least 2.1 V, at least 2.2 V, at least 2.3 V, at least 2.4 V, at least 2.5 V, at least 2.6 V, at least 2.7 V, at least 2.8 V, at least 2.9 V, at least 3.0 V, at least 3.1 V, at least 3.2 V, at least 3.3 V, at least 3.4 V, at least 3.5 V, at least 3.6 V, at least 3.7 V, at least 3.8 V, at least 3.9 V, at least 4.0 V, at least 4.1 V, at least 4.2 V, at least 4.3 V, at least 4.4 V, at least 4.5 V, at least 4.6 V, at least 4.7 V, at least 4.8 V, at least 4.9 V, at least 5.0 V, or the like.

In a particular embodiment, the difference of the standard potentials of the first and second reservoirs can be not more than 0.05 V, or not more than 0.06 V, not more than 0.07 V, not more than 0.08 V, not more than 0.09 V, not more than 0.1 V, not more than 0.2 V, not more than 0.3 V, not more than 0.4 V, not more than 0.5 V, not more than 0.6 V, not more than 0.7 V, not more than 0.8 V, not more than 0.9 V, not more than 1.0 V, not more than 1.1 V, not more than 1.2 V, not more than 1.3 V, not more than 1.4 V, not more than 1.5 V, not more than 1.6 V, not more than 1.7 V, not more than 1.8 V, not more than 1.9 V, not more than 2.0 V, not more than 2.1 V, not more than 2.2 V, not more than 2.3 V, not more than 2.4 V, not more than 2.5 V, not more than 2.6 V, not more than 2.7 V, not more than 2.8 V, not more than 2.9 V, not more than 3.0 V, not more than 3.1 V, not more than 3.2 V, not more than 3.3 V, not more than 3.4 V, not more than 3.5 V, not more than 3.6 V, not more than 3.7 V, not more than 3.8 V, not more than 3.9 V, not more than 4.0 V, not more than 4.1 V, not more than 4.2 V, not more than 4.3 V, not more than 4.4 V, not more than 4.5 V, not more than 4.6 V, not more than 47 V, not more than 4.8 V, not more than 4.9 V, not more than 5.0 V, or the like. In embodiments that include very small reservoirs (e.g., on the nanometer scale), the difference of the standard potentials can be substantially less or more. The electrons that pass between the first reservoir and the second reservoir can be generated as a result of the difference of the standard potentials.

The voltage present at the site of use of the system is typically in the range of millivolts but disclosed embodiments can introduce a much higher voltage, for example near 1 volt when using the 1 mm spacing of dissimilar metals already described. In this way the current not only can drive silver and zinc into the treatment if desired for treatment, but the current can also provide a stimulatory current so that the entire surface area can be treated. The electric field can also have beneficial effects on cell migration, ATP production, and angiogenesis.

A system or device disclosed herein can comprise an adhesive layer. In embodiments the adhesive layer can comprise a heat-activated adhesive. In embodiments the adhesive layer is located on the treatment (contact) side of the substrate layer. The adhesive layer can maintain the position of the device on or about the treatment area, for example the skin.

In embodiments, the adhesive layer can comprise, for example, a Hi-Tack elastic, a conformable tape provided and a white liner. In an embodiment, the adhesive layer can comprise 3M™ 9904 High Tack Elastic Nonwoven Fabric Medical Tape. In embodiments, the adhesive layer comprises a "cutout" to allow exudate or other fluid from a treatment area to pass from the substrate layer to the absorbent layer. In embodiments the adhesive layer can be hypoallergenic. In embodiments the adhesive layer can comprise an acrylate adhesive. In embodiments the adhesive layer can have a tensile strength of about 4 lbs/in of width. In embodiments the adhesive layer is located on the non-treatment side of the substrate layer. The adhesive layer can maintain the position of the device on or about the treatment area, for example the skin. In embodiments, the adhesive layer comprises a "cutout" to allow exudate or other fluid from a treatment area to pass from the substrate layer to an absorbent layer, for example foam.

A system or device disclosed herein can comprise an absorbent layer. In embodiments the absorbent layer is located on the adhesive layer on the side opposite the substrate layer. In embodiments, the absorbent layer comprises water, saline, or an active agent to maintain hydration in the substrate layer.

In embodiments the absorbent layer is located on the substrate layer. In embodiments, the absorbent comprises water, saline, or an active agent to maintain hydration in the substrate layer.

The absorbent layer can comprise, for example, a medical-grade foam. For example, in embodiments the foam is certified to comply with the ISO 10993 protocol. In an embodiment the absorbent layer can comprise 3M™ TEGA-DERM™, hydrophilic polyurethane foam, non-hydrophilic polyurethane foam, non-foam absorbents such as woven fabrics, non-woven fabrics made from polyester fibers, rayon fibers, cellulose-based fibers, superabsorbent fibers, combinations of multiple types of fibers, and the like.

A system or device disclosed herein can comprise a stretchable film layer. In embodiments the film layer can be breathable and stretchable. In embodiments the film layer is located on the absorbent layer on the side opposite the adhesive layer. In embodiments the film layer can comprise, a polymer, for example, polyurethane. The film layer encapsulates and seals the absorbent, providing room for the absorbent layer to expand as well as maintaining hydration in the absorbent layer and thus the substrate layer. In embodiments, the film layer can stretch or expand to allow for expansion of the absorbent layer.

Systems and devices disclosed herein can comprise complementary areas on, for example, their perimeter that complement other areas on the perimeter such that the areas engage with other areas on the device or with other devices by the fitting together of projections and recesses.

Embodiments disclosed herein can comprise a cosmetic product. For example, embodiments can comprise a skin care cream wherein the skin care cream is located between the skin and the electrode surface. Embodiments disclosed herein can comprise a cosmetic procedure. For example, embodiments can be employed before, after, or during a cosmetic procedure, such as before, after, or during a dermal filler injection. Certain embodiments can comprise use of a device disclosed herein before, after, or during a BOTOX® injection. Certain embodiments can comprise use of a device disclosed herein before, after, or during a resurfacing procedure.

In embodiments the system can comprise a port to access the interior of the absorbent layer, for example to add hydration, active agents, carriers, solvents, or some other material. Certain embodiments can comprise a "blister" top that can enclose a material such as an antibacterial. In embodiments the blister top can contain a material that is released into or on to the material when the blister is pressed, for example a liquid or cream. For example, embodiments disclosed herein can comprise a blister top containing an antibacterial or the like.

In embodiments the system comprises a component such as elastic or other such fabric to maintain or help maintain its position. In embodiments the system comprises components such as straps to maintain or help maintain its position. In certain embodiments the system or device comprises a strap on either end of the long axis, or a strap linking on end of the long axis to the other. In embodiments that straps can comprise Velcro or a similar fastening system. In embodiments the straps can comprise elastic materials. In embodiments the hydrogel can be configured into straps as a part of the material. In further embodiments, the strap can comprise a conductive material, for example a wire to electrically link the device with other components, such as monitoring equipment or a power source. In embodiments the device can be wirelessly linked to monitoring or data collection equipment, for example linked via Bluetooth to a cell phone or computer that collects data from the device. In certain embodiments the device can comprise data collection means, such as temperature, pH, pressure, or conductivity data collection means.

In embodiments the positioning component can comprise an elastic film with an elasticity similar to that of skin, or greater than that of skin, or less than that of skin. In embodiments, the system can comprise a laminate where layers of the laminate can be of varying elasticities. For example, an outer layer may be highly elastic and an inner layer in-elastic or less elastic. The in-elastic layer can be made to stretch by placing stress relieving discontinuous regions through the thickness of the material so there is a mechanical displacement rather than stress that would break the hydrogel before stretching would occur. In embodiments the stress relieving discontinuous regions can extend completely through a layer or the system or can be placed where expansion is required. In embodiments of the system the stress relieving discontinuous regions do not extend all the way through the system or a portion of the system such as the substrate. In embodiments the discontinuous regions can pass halfway through the long axis of the substrate.

Devices and systems disclosed herein can comprise "anchor" regions or "arms" or straps to affix the system securely. The anchor regions or arms can anchor the system. For example, a system can be secured to an area proximal to a joint or irregular skin surface, and anchor regions of the system can extend to areas of minimal stress or movement to securely affix the system. Further, the system can reduce stress on an area, for example by "countering" the physical stress caused by movement.

In embodiments the system or device can comprise additional materials to aid in treatment.

In embodiments, the system or device can comprise instructions or directions on how to place the system to maximize its performance. Embodiments comprise a kit comprising a system and directions for its use. For example, embodiments can include a treatment protocol, such as a dressing replacement schedule.

In certain embodiments dissimilar metals can be used to create an electric field with a desired voltage within the device or system. In certain embodiments the pattern of reservoirs can control the watt density and shape of the electric field.

Certain embodiments can utilize a power source to create the electric current, such as a battery or a micro-battery. The power source can be any energy source capable of generating a current in the system and can comprise, for example, AC power, DC power, radio frequencies (RF) such as pulsed RF, induction, ultrasound, and the like.

Dissimilar metals used to make a system or device disclosed herein can be, for example, silver and zinc. In certain embodiments the electrodes are coupled with a non-conductive material to create a random dot pattern or a uniform dot pattern within a hydrogel, most preferably an array or multi-array of voltaic cells that do not spontaneously react until they contact an electrolytic solution. Sections of this description use the terms "coated," "plated," or "printed" with "ink," but it is to be understood that a dot in a hydrogel may also be a solid microsphere of conductive material. The use of any suitable means for applying a conductive material is contemplated. In embodiments "coated," "plated," or "printed" can comprise any material such as a solution suitable for forming an electrode on a surface of a microsphere such as a conductive material comprising a conductive metal solution.

In another embodiment, "coated," "plated," or "printed" can comprise electroplating microspheres. Electroplating is a process that uses electric current to reduce dissolved metal cations so that they form a coherent metal coating on an electrode. Electroplating can be used to change the surface properties of microspheres or to build up thickness of a microsphere. Building thickness by electroplating microspheres can allow the microspheres to be form with a specific conductive material and at a specific gravity determined by the user.

In embodiments, printing devices can be used to produce systems and devices as disclosed herein. For example, inkjet or "3D" printers can be used to produce embodiments. In certain embodiments the binders or inks used to produce iontophoresis systems disclosed herein can comprise, for example, poly cellulose inks, poly acrylic inks, poly urethane inks, silicone inks, and the like. In embodiments the type of ink used can determine the release rate of electrons from the reservoirs. In embodiments various materials can be added to the ink or binder such as, for example, conductive or resistive materials can be added to alter the shape or strength of the electric field. Other materials, such as silicon, can be added. Such materials can also be added to the spaces between reservoirs.

In certain embodiments, the system or device can be shaped to fit a particular region of the body.

Embodiments disclosed herein can comprise interlocking perimeter areas that complement other areas on the perimeter such that the areas engage with each other by the fitting together of projections or protrusions and recesses or intrusions. Such embodiments provide several advantages, for example additional securing force for the device, as well as allowing a user to custom-fit the device over a specific area. This allows the administration of a tailored electric field to a particular area, for example a uniform electric field or a field of varying strength. In embodiments, multiple port sites or scope sites can be accommodated. In embodiments, these multiple port or scope sites can be provided without device overlap, but still providing complete coverage of the area where treatment is desired. Multiple port sites can be useful in embodiments used with adjunctive wound therapies, for example Negative Pressure Wound Therapy (NPWT) or Topical Oxygen Therapy (TOT). The port or scope sites can also be useful for accessing an injury, for example for use in arthroscopic surgery. The port or scope sites can comprise, for example, a void region in the substrate, or "slits" defining a section of the substrate such that the substrate can be peeled back to access the tissue beneath.

Certain embodiments disclosed herein comprise a method of manufacturing a LLEC or LLEF system, the method comprising coupling a substrate with one or more biocompatible electrodes configured to generate at least one of a low level electric field or low level electric current. The substrate can be planar. In another embodiment, the method comprises joining a substrate with one or more biocompatible electrodes comprising a first bioelectric element comprising a first microparticle formed from a first conductive material, and a second bioelectric element comprising a second microparticle formed from a second conductive material. For example, the first microparticle formed from a first conductive material can be a reducing agent. The second microparticle formed from a second conductive material can be an oxidizing agent.

Embodiments disclosed herein comprise iontophoresis systems that can produce an electrical stimulus and/or can electromotivate, electroconduct, electroinduct, electrotransport, and/or electrophorese one or more therapeutic materials in areas of target tissue (e.g., iontophoresis), and/or can cause one or more biologic or other materials in proximity to, on or within target tissue to be rejuvenated.

In certain embodiments, for example treatment methods, it can be preferable to utilize AC or DC current. For example, embodiments disclosed herein can employ phased array, pulsed, square wave, sinusoidal, or other wave forms, combinations, or the like. Certain embodiments utilize a controller to produce and control power production and/or distribution to the device.

Embodiments disclosed herein relating to treatment can also comprise selecting a patient or tissue in need of, or that could benefit by, using a disclosed system.

While various embodiments have been shown and described, it will be realized that alterations and modifications can be made thereto without departing from the scope of the following claims. It is expected that other methods of applying the conductive material can be substituted as appropriate. Also, there are numerous shapes, sizes and patterns of voltaic cells that have not been described but it is expected that this disclosure will enable those skilled in the art to incorporate their own designs which will then which will become active when brought into contact with an electrolytic solution.

Methods of Use

Methods disclosed herein can comprise applying a disclosed embodiment to an area to be treated. Embodiments can comprise selecting or identifying a patient in need of treatment, for example a patient who has received surgical treatment of a joint. In embodiments, methods disclosed herein can comprise formation and application of a system or device disclosed herein to an area to be treated.

Embodiments can comprise treatment of a joint after surgery, for example epicondylitis correction surgery, joint replacement, arthritis treatment, or the like. Embodiments can comprise treatment following arthroscopy, joint resurfacing, osteotomy, arthrodesis, total joint replacement (TJR), minimally invasive TJR, joint revision, tendonitis, dislocations, fractures, ulnar collateral ligament reconstruction, fractures, removal of loose bodies, or the like.

Joints that can be treated with the systems, methods, and devices disclosed herein can comprise, for example, balland-socket joints, hinge joints, pivot joints, ellipsoidal joints, saddle joints, and the like.

In embodiments, disclosed methods comprise application to the treatment area or the device of a system disclosed herein comprising an active agent.

Embodiments can comprise selecting or identifying a patient in need of treatment, for example a patient who has received an abrasion, for example as a result of a bicycle accident. In embodiments, methods disclosed herein can comprise formation and application of a system or device disclosed herein to an area to be treated, for example to the patient's back, buttocks, hip, or forearm.

In embodiments the active agent can be, for example, positively or negatively charged. In embodiments, positively charged active agents can comprise centbucridine, tetracaine, Novocaine® (procaine), ambucaine, amolanone, amylcaine, benoxinate, betoxycaine, carticaine, chloroprocaine, cocaethylene, cyclomethycaine, butethamine, butoxycaine, carticaine, dibucaine, dimethisoquin, dimethocaine, diperodon, dyclonine, ecogonidine, ecognine, euprocin, fenalcomine, formocaine, hexylcaine, hydroxyteteracaine, leucinocaine, levoxadrol, metabutoxycaine, myrtecaine, butamben, bupivicaine, mepivacaine, beta-adrenoceptor antagonists, opioid analgesics, butanilicaine, ethyl aminobenzoate, fomocine, hydroxyprocaine, isobutyl p-aminobenzoate, naepaine, octacaine, orthocaine, oxethazaine, parenthoxycaine, phenacine, phenol, piperocaine, polidocanol, pramoxine, prilocalne, propanocaine, proparacaine, propipocaine, pseudococaine, pyrrocaine, salicyl alcohol, parethyoxycaine, piridocaine, risocaine, tolycaine, trimecaine, tetracaine, anticonvulsants, antihistamines, articaine, cocaine, procaine, amethocaine, chloroprocaine, marcaine, chloroprocaine, etidocaine, prilocaine, lignocaine, benzocaine, zolamine, ropivacaine, and dibucaine, dexamethasone phosphate, combinations thereof.

EXAMPLES

The following non-limiting example is provided for illustrative purposes only in order to facilitate a more complete understanding of representative embodiments. This example should not be construed to limit any of the embodiments described in the present specification.

Example 1

Cell Migration Assay

The in vitro scratch assay is an easy, low-cost and well-developed method to measure cell migration in vitro. The basic steps involve creating a "scratch" in a cell monolayer, capturing images at the beginning and at regular intervals during cell migration to close the scratch, and comparing the images to quantify the migration rate of the cells. Compared to other methods, the in vitro scratch assay is particularly suitable for studies on the effects of cell-matrix and cell-cell interactions on cell migration, mimic cell migration during wound healing in vivo and are compatible with imaging of live cells during migration to monitor intracellular events if desired. In addition to monitoring migration of homogenous cell populations, this method has also been adopted to measure migration of individual cells in the leading edge of the scratch. Not taking into account the time for transfection of cells, in vitro scratch assay per se usually takes from several hours to overnight.

Human keratinocytes were plated under plated under placebo or a LLEC system (substrate layer as described herein; "PROCELLERA®"). Cells were also plated under silver-only or zinc-only dressings. After 24 hours, the scratch assay was performed. Cells plated under the PROCELLERA® device displayed increased migration into the "scratched" area as compared to any of the zinc, silver, or placebo dressings. After 9 hours, the cells plated under the PROCELLERA® device had almost "closed" the scratch. This demonstrates the importance of electrical activity to cell migration and infiltration.

In addition to the scratch test, genetic expression was tested. Increased insulin growth factor (IGF)-1R phosphorylation was demonstrated by the cells plated under the PROCELLERA® device as compared to cells plated under insulin growth factor alone.

Integrin accumulation also affects cell migration. An increase in integrin accumulation was achieved with the LLEC system. Integrin is necessary for cell migration, and is found on the leading edge of migrating cell.

Thus, the tested LLEC system enhanced cellular migration and IGF-1R/integrin involvement. This involvement demonstrates the effect that the LLEC system had upon cell receptors involved with the wound healing process.

Example 2

Zone of Inhibition Test

For cellular repair to be most efficient, available energy should not be shared with ubiquitous microbes. In this "zone of inhibition" test, placebo, a LLEC device (substrate layer as described herein; PROCELLERA®) and silver only were tested in an agar medium with a 24 hour growth of organisms. Bacteria grew over the placebo, there was a zone of inhibition over the PROCELLERA® and a minimal inhibition zone over the silver. Because the samples were "buried" in agar, the electricidal effect of the LLEC system could be tested. This could mean the microbes were affected by the electrical field or the silver ion transport through the agar was enhanced in the presence of the electric field. Silver ion diffusion, the method used by silver based antimicrobials, alone was not sufficient. The test demonstrates the improved bactericidal effect of PROCELLERA® as compared to silver alone.

Example 3

Wound Care Study

The medical histories of patients who received "standard-of-care" wound treatment ("SOC"; n=20), or treatment with a LLEC substrate as disclosed herein (n=18), were reviewed. The wound care device used in the present study consisted of a discrete matrix of silver and zinc dots. A sustained voltage of approximately 0.8 V was generated between the dots. The electric field generated at the device surface was measured to be 0.2-1.0 V, 10-50 µA.

Wounds were assessed until closed or healed. The number of days to wound closure and the rate of wound volume reduction were compared. Patients treated with LLEC substrate received one application of the device each week, or more frequently in the presence of excessive wound exudate, in conjunction with appropriate wound care management. The LLEC substrate was kept moist by saturating with normal saline or conductive hydrogel. Adjunctive therapies (such as negative pressure wound therapy [NPWT], etc.) were administered with SOC or with the use of the LLEC substrate unless contraindicated. The SOC group received the standard of care appropriate to the wound, for example antimicrobial dressings, barrier creams, alginates, silver dressings, absorptive dressings, hydrogel, enzymatic debridement ointment, NPWT, etc. Etiology-specific care was administered on a case-by-case basis. Dressings were applied at weekly intervals or more. The SOC and LLEC groups did not differ significantly in gender, age, wound types or the length, width, and area of their wounds.

Wound dimensions were recorded at the beginning of the treatment, as well as interim and final patient visits. Wound dimensions, including length (L), width (W) and depth (D) were measured, with depth measured at the deepest point. Wound closure progression was also documented through digital photography. Determining the area of the wound was performed using the length and width measurements of the wound surface area.

Closure was defined as 100% epithelialization with visible effacement of the wound. Wounds were assessed 1 week post-closure to ensure continued progress toward healing during its maturation and remodeling phase.

Wound types included in this study were diverse in etiology and dimensions, thus the time to heal for wounds was distributed over a wide range (9-124 days for SOC, and 3-44 days for the LLEC group). Additionally, the patients often had multiple co-morbidities, including diabetes, renal disease, and hypertension. The average number of days to wound closure was 36.25 (SD=28.89) for the SOC group and 19.78 (SD=14.45) for the LLEC group, p=0.036. On average, the wounds in the LLEC treatment group attained closure 45.43% earlier than those in the SOC group.

Based on the volume calculated, some wounds improved persistently while others first increased in size before improving. The SOC and the LLEC groups were compared to each other in terms of the number of instances when the dimensions of the patient wounds increased (i.e., wound treatment outcome degraded). In the SOC group, 10 wounds (50% for n=20) became larger during at least one measurement interval, whereas 3 wounds (16.7% for n=18) became larger in the LLEC group (p=0.018). Overall, wounds in both groups responded positively. Response to treatment was observed to be slower during the initial phase, but was observed to improve as time progressed.

The LLEC wound treatment group demonstrated on average a 45.4% faster closure rate as compared to the SOC group. Wounds receiving SOC were more likely to follow a "waxing-and-waning" progression in wound closure compared to wounds in the LLEC treatment group.

Compared to localized SOC treatments for wounds, the LLEC (1) reduces wound closure time, (2) has a steeper wound closure trajectory, and (3) has a more robust wound healing trend with fewer incidence of increased wound dimensions during the course of healing.

Example 4

LLEC Influence on Human Keratinocyte Migration

An LLEC-generated electrical field was mapped, leading to the observation that LLEC generates hydrogen peroxide, known to drive redox signaling. LLEC-induced phosphorylation of redox-sensitive IGF-1R was directly implicated in cell migration. The LLEC also increased keratinocyte mitochondrial membrane potential.

The LLEC substrate was made of polyester printed with dissimilar elemental metals. It comprises alternating circular regions of silver and zinc dots, along with a proprietary, biocompatible binder added to lock the electrodes to the surface of a flexible substrate in a pattern of discrete reservoirs. When the LLEC contacts an aqueous solution, the silver positive electrode (cathode) is reduced while the zinc negative electrode (anode) is oxidized. The LLEC used herein consisted of metals placed in proximity of about 1 mm to each other thus forming a redox couple and generating an ideal potential on the order of 1 Volt. The calculated values of the electric field from the LLEC were consistent with the magnitudes that are typically applied (1-10 V/cm) in classical electrotaxis experiments, suggesting that cell migration observed with the bioelectric dressing is likely due to electrotaxis.

Measurement of the potential difference between adjacent zinc and silver dots when the LLEC is in contact with de-ionized water yielded a value of about 0.2 Volts. Though the potential difference between zinc and silver dots can be measured, non-intrusive measurement of the electric field arising from contact between the LLEC and liquid medium was difficult. Keratinocyte migration was accelerated by exposure to an Ag/Zn LLEC. Replacing the Ag/Zn redox couple with Ag or Zn alone did not reproduce the effect of keratinocyte acceleration.

Exposing keratinocytes to an LLEC for 24 h significantly increased green fluorescence in the dichlorofluorescein (DCF) assay indicating generation of reactive oxygen species under the effect of the LLEC. To determine whether $H_2O_2$ is generated specifically, keratinocytes were cultured with a LLEC or placebo for 24 h and then loaded with PF6-AM (Peroxyfluor-6 acetoxymethyl ester; an indicator of endogenous $H_2O_2$). Greater intracellular fluorescence was observed in the LLEC keratinocytes compared to the cells grown with placebo. Over-expression of catalase (an enzyme that breaks down $H_2O_2$) attenuated the increased migration triggered by the LLEC. Treating keratinocytes with N-Acetyl Cysteine (which blocks oxidant-induced signaling) also failed to reproduce the increased migration observed with LLEC. Thus, $H_2O_2$ signaling mediated the increase of keratinocyte migration under the effect of the electrical stimulus.

External electrical stimulus can up-regulate the TCA (tricarboxylic acid) cycle. The stimulated TCA cycle is then expected to generate more NADH and FADH 2 to enter into the electron transport chain and elevate the mitochondrial membrane potential ($\Delta m$). Fluorescent dyes JC-1 and TMRM were used to measure mitochondrial membrane potential. JC-1 is a lipophilic dye which produces a red fluorescence with high $\Delta m$ and green fluorescence when $\Delta m$ is low. TMRM produces a red fluorescence proportional to $\Delta m$. Treatment of keratinocytes with LLEC for 24 h demonstrated significantly high red fluorescence with both JC-1 and TMRM, indicating an increase in mitochondrial membrane potential and energized mitochondria under the effect of the LLEC. As a potential consequence of a stimulated TCA cycle, available pyruvate (the primary substrate for the TCA cycle) is depleted resulting in an enhanced rate of glycolysis. This can lead to an increase in glucose uptake in order to push the glycolytic pathway forward. The rate of glucose uptake in HaCaT cells treated with LLEC was examined next. More than two fold enhancement of basal glucose uptake was observed after treatment with LLEC for 24 h as compared to placebo control.

Keratinocyte migration is known to involve phosphorylation of a number of receptor tyrosine kinases (RTKs). To determine which RTKs are activated as a result of LLEC, scratch assay was performed on keratinocytes treated with LLEC or placebo for 24 h. Samples were collected after 3 h and an antibody array that allows simultaneous assessment of the phosphorylation status of 42 RTKs was used to quantify RTK phosphorylation. It was determined that LLEC significantly induces IGF-1R phosphorylation. Sandwich ELISA using an antibody against phospho-IGF-1R and total IGF-1R verified this determination. As observed with the RTK array screening, potent induction in phosphorylation of IGF-1R was observed 3 h post scratch under the influence of LLEC. IGF-1R inhibitor attenuated the increased keratinocyte migration observed with LLEC treatment.

MBB (monobromobimane) alkylates thiol groups, displacing the bromine and adding a fluorescent tag (lamda emission=478 nm). MCB (monochlorobimane) reacts with only low molecular weight thiols such as glutathione. Fluorescence emission from UV laser-excited keratinocytes loaded with either MBB or MCB was determined for 30 min. Mean fluorescence collected from 10,000 cells showed a significant shift of MBB fluorescence emission from cells. No significant change in MCB fluorescence was observed, indicating a change in total protein thiol but not glutathione. HaCaT cells were treated with LLEC for 24 h followed by a scratch assay. Integrin expression was observed by immuno-cytochemistry at different time points. Higher integrin expression was observed 6 h post scratch at the migrating edge.

Consistent with evidence that cell migration requires $H_2O_2$ sensing, we determined that by blocking $H_2O_2$ signaling by decomposition of $H_2O_2$ by catalase or ROS scavenger, N-acetyl cysteine, the increase in LLEC-driven cell migration is prevented. The observation that the LLEC increases $H_2O_2$ production is significant because in addition to cell migration, hydrogen peroxide generated in the wound margin tissue is required to recruit neutrophils and other leukocytes to the wound, regulates monocyte function, and VEGF signaling pathway and tissue vascularization. Therefore, external electrical stimulation can be used as an effective strategy to deliver low levels of hydrogen peroxide over time to mimic the environment of the healing wound and thus should help improve wound outcomes. Another phenomenon observed during re-epithelialization is increased expression of the integrin subunit ay. There is evidence that integrin, a major extracellular matrix receptor, polarizes in response to applied ES and thus controls directional cell migration. It may be noted that there are a number of integrin subunits, however we chose integrin αv because of evidence of association of αv integrin with IGF-1R, modulation of IGF-1 receptor signaling, and of driving keratinocyte locomotion. Additionally, integrin αv has been reported to contain vicinal thiols that provide site for redox activation of function of these integrins and therefore the increase in protein thiols that we observe under the effect of ES may be the driving force behind increased integrin mediated cell migration. Other possible integrins which may be playing a role in LLEC-induced IGF-1R mediated keratinocyte migration are α5 integrin and α6 integrin.

Materials and Methods

Cell culture—Immortalized HaCaT human keratinocytes were grown in Dulbecco's low-glucose modified Eagle's medium (Life Technologies, Gaithersburg, MD, U.S.A.) supplemented with 10% fetal bovine serum, 100 U/ml penicillin, and 100 µg/ml streptomycin. The cells were maintained in a standard culture incubator with humidified air containing 5% $CO_2$ at 37° C.

Scratch assay—A cell migration assay was performed using culture inserts (IBIDI®, Verona, WI) according to the manufacturers instructions. Cell migration was measured using time-lapse phase-contrast microscopy following withdrawal of the insert. Images were analyzed using the AxioVision Rel 4.8 software.

N-Acetyl Cysteine Treatment—Cells were pretreated with 5 mM of the thiol antioxidant N-acetylcysteine (Sigma) for 1 h before start of the scratch assay.

IGF-1R inhibition—When applicable, cells were preincubated with 50 nM IGF-1R inhibitor, picropodophyllin (Calbiochem, MA) just prior to the Scratch Assay.

Cellular $H_2O_2$ Analysis—To determine intracellular $H_2O_2$ levels, HaCaT cells were incubated with 5 pM PF6-AM in PBS for 20 min at room temperature. After loading, cells were washed twice to remove excess dye and visualized using a Zeiss Axiovert 200M microscope.

Catalase gene delivery—HaCaT cells were transfected with $2.3 \times 10^7$ pfu AdCatalase or with the empty vector as control in 750 µL of media. Subsequently, 750 µL of additional media was added 4 h later and the cells were incubated for 72 h.

RTK Phosphorylation Assay—Human Phospho-Receptor Tyrosine Kinase phosphorylation was measured using Phospho-RTK Array kit (R & D Systems).

ELISA—Phosphorylated and total IGF-1R were measured using a DuoSet IC ELISA kit from R&D Systems.

Determination of Mitochondrial Membrane Potential—Mitochondrial membrane potential was measured in HaCaT cells exposed to the LLEC or placebo using TMRM or JC-1 (MitoProbe JC-1 Assay Kit for Flow Cytometry, Life Technologies), per manufacturers instructions for flow cytometry.

Integrin αV Expression—Human HaCaT cells were grown under the MCD or placebo and harvested 6 h after removing the IBIDI® insert. Staining was done using antibody against integrin αV (Abcam, Cambridge, MA).

Example 5

Generation of Superoxide

A LLEC substrate was tested to determine the effects on superoxide levels which can activate signal pathways. PROCELLERA® LLEC substrate increased cellular protein sulfhydryl levels. Further, the PROCELLERA® substrate increased cellular glucose uptake in human keratinocytes. Increased glucose uptake can result in greater mitochondrial activity and thus increased glucose utilization, providing more energy for cellular migration and proliferation. This can speed wound healing.

Example 6

Treatment of Lateral Epicondylitis

Figure 20B:
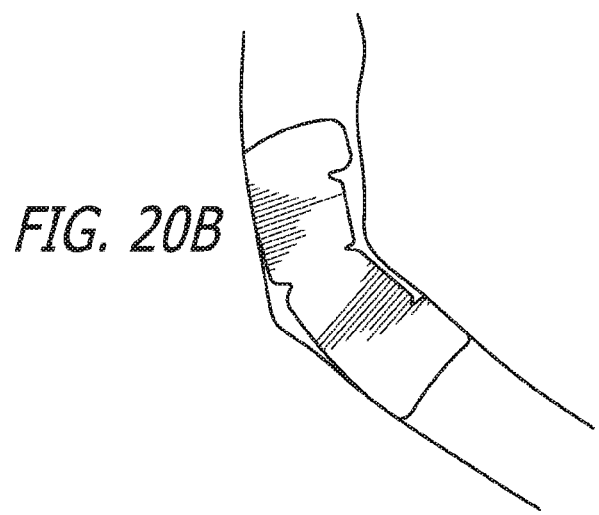
Figure 20C:
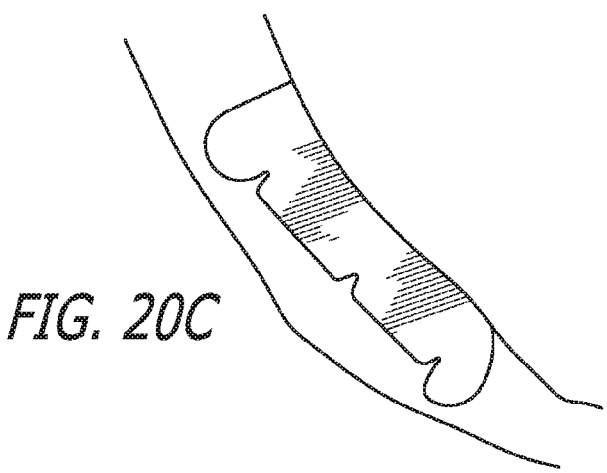

A 29 year-old tennis player reports pain on the outside of her elbow. Her doctor performs arthroscopic surgery to correct the damaged tissue. Following surgery, an embodiment as disclosed (and seen in FIGS. 13 and 20) herein is applied to the patient's elbow to stimulate healing and prevent post-surgical infection.

Example 7

Treatment of Medial Epicondylitis

Figure 21A:
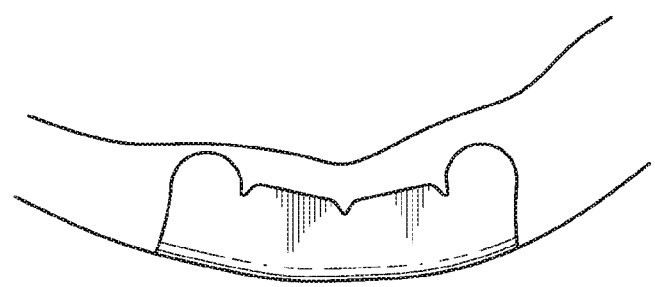
FIGS. 21A-21B depict the embodiments of FIGS. 18 and 19 as applied to a patient's elbow.
Figure 21B:
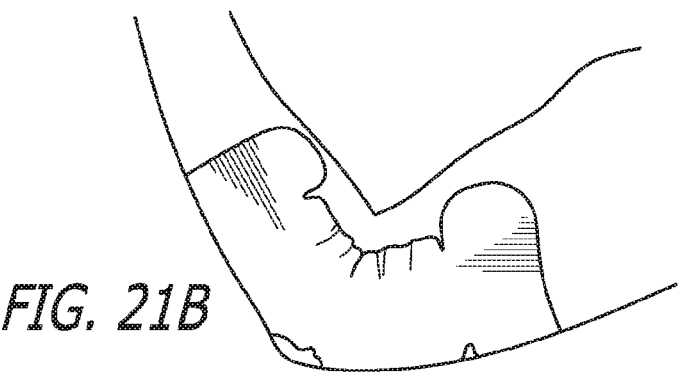
Figure 22A:
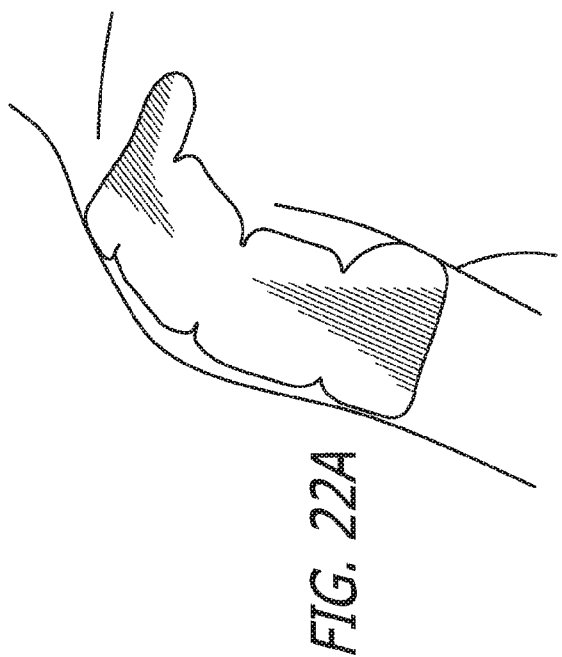
FIGS. 22A-22D depict the embodiments of FIGS. 18 and 19 as applied to a patient's shoulder.
Figure 22B:
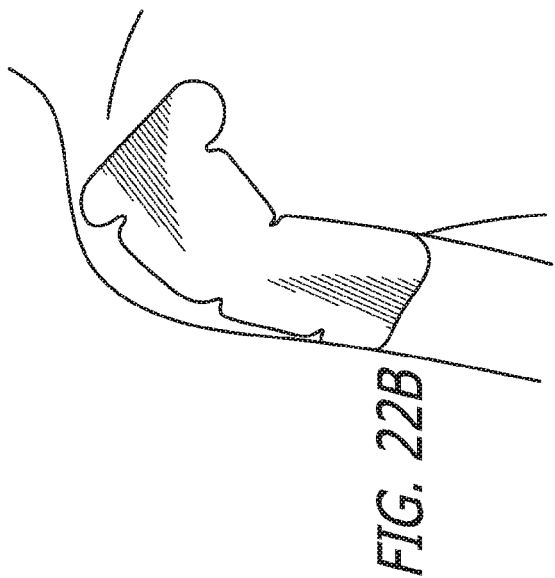
Figure 22C:
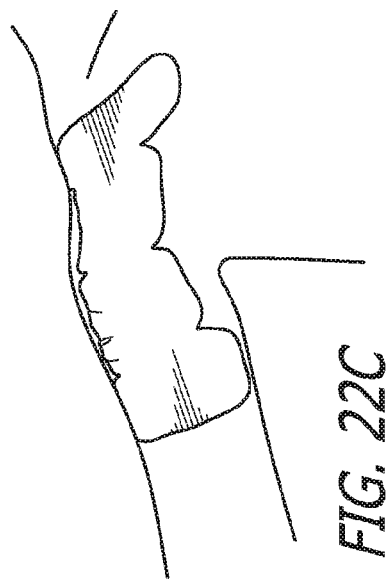
Figure 22D:
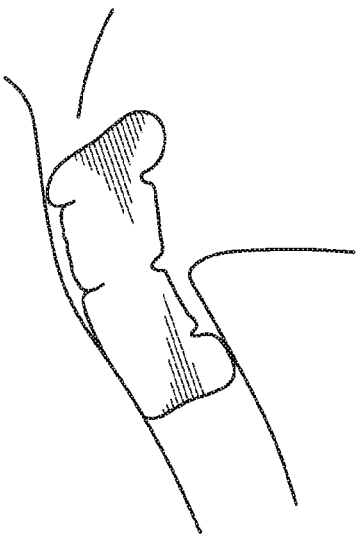

A 42 year-old golfer reports pain on the inside of his elbow. His doctor performs arthroscopic surgery to correct the damaged tissue. Following surgery, an embodiment as disclosed (and seen in FIGS. 14 and 21) herein is applied to the patient's elbow to stimulate healing and prevent post-surgical infection.

Example 8

Treatment of Medial Epicondylitis

A 59 year-old golfer reports pain on the inside of his elbow. His doctor recommends rest, physical therapy, and use of an embodiment as disclosed (and seen in FIGS. 14 and 21) to stimulate healing of the affected tissue.

Example 9

Treatment Following Knee Replacement

A 84 year-old male undergoes knee replacement surgery. Following the procedure, the doctor applies a wound dressing designed for the knee as described herein (and seen in FIG. 8) The dressing stimulates healing and prevents post-surgical infection while providing full articulation of the joint and avoiding excess shear force on the surrounding skin.

Example 10

Treatment Following Hip Replacement

A 84 year-old male undergoes hip replacement surgery. Following the procedure, the doctor applies a wound dressing designed for the hip as described herein. The dressing stimulates healing and prevents post-surgical infection while providing full articulation of the joint and avoiding excess shear force on the surrounding skin.

Example 11

Treating Knee Lacerations

A 17 year-old boy injures his knee playing football. The emergency room doctor cleans the lacerations then applies a composite wound dressing as described herein. The composite wound dressing with a substrate comprising a multi-array matrix of biocompatible microcells fits over the lacerations. The expandable absorbent layer prevents excessive fluid buildup in the wound as the layer stretches away from the wound, and reduces the potential for peg-wound skin maceration and/or shear force on the surrounding skin. After a month, the knee has healed with very little visible scarring.

Example 12

Treatment of a Full-Thickness Elbow Wound

A 35-year old male suffers from a full-thickness wound to his elbow. The burn is debrided, then to the wound is applied a composite wound dressing as described herein. The dressing includes ports through which to drain the wound. The system is used to cover the wound. The expandable absorbent layer prevents excessive fluid buildup in the wound and reduces the potential for peri-wound skin maceration and/or shear force on the surrounding skin. The system includes a "peel-back" mechanism to allow access to the wound site without removing the dressing. The burn heals without the need for skin grafts.

Example 13

Treatment of Road Rash

A 34 year-old cyclist crashes his bicycle, causing "road rash" on his leg, arm, shoulder, and back. A universal dressing as disclosed herein (and seen in FIG. 15) is applied in various orientations such that it comfortably fits and contours to each of the wound locations (as seen in FIG. 17). The "arms" of the dressing secure it in place while minimizing shear force on the surrounding skin. The dressing stimulates healing and prevents infection. After a month, the back has healed with very little visible scarring.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, comprising the best mode known to the inventor for carrying out the methods and devices described herein. Of course, variations on these described embodiments will become apparent to those of ordinary skill in the art upon reading the foregoing description. Accordingly, this disclosure comprises all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be comprised in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

The invention claimed is:

1. A method for treating a joint of the body, comprising affixing to the joint a bioelectric device comprising an absorbent layer and a substrate layer comprising two or more biocompatible electrodes configured to generate at least one of; a uniform low level electric field (LLEF); or a uniform low level electric current (LLEC);
    wherein the device further comprises a port to provide access to the absorbent layer, and wherein the biocompatible electrodes comprise a first array comprising a pattern of microcells formed from a first conductive material, and a second array comprising a pattern of microcells formed from a second conductive material, and the first array and the second array spontaneously generate a LLEF.

2. The method of claim 1, wherein the first array and the second array spontaneously generate a LLEC when contacted with an electrolytic solution or with a conductive fluid.

3. The method of claim 2 wherein the uniform LLEC is between 1 and 200 micro-amperes.

4. The method of claim 3 wherein the uniform LLEC is between 1 and 100 micro-amperes.

5. The method of claim 3 wherein the uniform LLEC is between 100 and 200 micro-amperes.

6. The method of claim 3 wherein the uniform LLEC is between 150 and 200 micro-amperes.

7. The method of claim 1, wherein the LLEF is between 0.05 and 5 Volts.

8. The method of claim 7 wherein the LLEF is between 0.1 and 5 Volts.

9. The method of claim 7 wherein the LLEF is between 1.0 and 5 Volts.

10. The method of claim 1 wherein the substrate comprises a pliable material.

11. The method of claim 1 wherein said joint comprises the wrist.

12. The method of claim 1 wherein said joint comprises the knee.

13. The method of claim 1 wherein said joint comprises the elbow.

14. The method of claim 1 wherein said joint comprises the shoulder.

* * * * *